(12) United States Patent
Cox et al.

(10) Patent No.: US 7,130,835 B2
(45) Date of Patent: Oct. 31, 2006

(54) SYSTEM AND METHOD FOR PREDICTIVE OPHTHALMIC CORRECTION

(75) Inventors: Ian G. Cox, Honeoye Falls, NY (US); Barry T. Eagan, Salt Lake City, UT (US); Howard Markman, Honeoye, NY (US); Kamal Sarbadhikari, Penfield, NY (US); Kristian Hohla, Vaterstetten (DE); Gerhard Youssefi, Landshut (DE); Craig Schoof, Sammamish, WA (US)

(73) Assignee: Bausch & Lomb Incorporated, Rochester, NY (US)

( * ) Notice: Subject to any disclaimer, the term of this patent is extended or adjusted under 35 U.S.C. 154(b) by 460 days.

(21) Appl. No.: 10/327,229

(22) Filed: Dec. 20, 2002

(65) Prior Publication Data

US 2004/0054358 A1 Mar. 18, 2004

Related U.S. Application Data

(60) Provisional application No. 60/368,643, filed on Mar. 28, 2002, provisional application No. 60/340,292, filed on Dec. 14, 2001.

(51) Int. Cl.
*A61B 18/18* (2006.01)
*G06F 15/18* (2006.01)

(52) U.S. Cl. .................... 706/21; 606/4; 606/5
(58) Field of Classification Search .......... 606/5, 606/4; 706/21
See application file for complete search history.

(56) References Cited

U.S. PATENT DOCUMENTS

| 5,777,719 | A | | 7/1998 | Williams .................. 351/212 |
|---|---|---|---|---|
| 5,891,131 | A | * | 4/1999 | Rajan et al. .................. 606/5 |
| 6,582,078 | B1 | * | 6/2003 | Halpern et al. ............. 351/205 |
| 6,726,680 | B1 | * | 4/2004 | Knopp et al. ................. 606/12 |
| 2002/0007176 | A1 | * | 1/2002 | Campin et al. ................ 606/5 |
| 2002/0026181 | A1 | * | 2/2002 | O'Donnell, Jr. ............. 606/10 |
| 2002/0065758 | A1 | * | 5/2002 | Henley ........................ 705/37 |
| 2002/0103479 | A1 | * | 8/2002 | Sarver ........................ 606/4 |
| 2003/0028115 | A1 | * | 2/2003 | Thomas ...................... 600/476 |
| 2003/0073931 | A1 | * | 4/2003 | Boecker et al. ............. 600/573 |
| 2003/0208190 | A1 | * | 11/2003 | Roberts et al. ................ 606/5 |

FOREIGN PATENT DOCUMENTS

| WO | 00/45759 | | 2/2000 |
|---|---|---|---|
| WO | WO 45759 A1 | * | 8/2000 |
| WO | 02/07660 | | 1/2002 |

OTHER PUBLICATIONS

U.S. Appl. No. 60/284,644 Entitled "Objective Manifest Refraction" filed Apr. 18, 2001 by Youssefi, et al.
U.S. Appl. No. 60/340,292 Entitled "Cornea Ultra Structural Model" filed Dec. 14, 2001 by Turner.

* cited by examiner

*Primary Examiner*—Anthony Knight
*Assistant Examiner*—Ronald E. Williams, Jr.

(57) ABSTRACT

A system and method for providing a predictive outcome in the form of a predictive best instruction for a therapeutic ophthalmic correction of a patient's vision defects. The predictive best instruction is derived from prospective therapeutic-outcome-influencing, new information that is analyzed in conjunction with optimized, historical therapeutic-outcome information. The instruction is preferably an optimized, custom, photoablative algorithm for driving a photoablative, excimer laser. The instruction can be provided on a fee basis.

63 Claims, 19 Drawing Sheets

SYSTEM AND METHOD FOR PREDICTIVE OPHTHALMIC CORRECTION

This application claims priority to U.S. Provisional application Ser. No. 60/368,643 filed on Mar. 28, 2002 and to U.S. Provisional application Ser. No. 60/340,292 filed on Dec. 14, 2001, both of which disclosures are fully incorporated by reference herein.

BACKGROUND OF THE INVENTION

1. Field of the Invention

The present invention relates generally to technology and business solutions directed to the correction of ophthalmic defects. In particular, the invention describes systems, instructions, and methods directed to providing a predictive outcome for therapeutic ophthalmic correction of vision disorders. The invention is intended to provide a higher degree of patient vision quality resulting from vision correction procedures.

2. Description of Related Art

A large percentage of the population have vision defects that are commonly referred to as myopia (near-sightedness) and hyperopia (far-sightedness), sometimes with an accompanying defect know as astigmatism. Myopia and hyperopia are the result of a lower-order optical aberration called defocus. Simple astigmatism is also a lower-order aberration. Briefly, a perfectly myopic eye brings all incoming parallel light to a focal point in front of the retina; a perfectly hyperopic eye brings all incoming parallel light to a focal point behind the retina; and a simply astigmatic eye focuses some of the light in a horizontal line and some of the light in a vertical line at some separation distances from the retina.

For a long time, practitioners have attempted to accurately measure these defects and correct them with spectacles, contact lenses, and other devices and/or procedures. Popular therapeutic procedures were, and continue to be, developed that use a suitable laser beam (typically, an excimer laser having a wavelength of 193 nm) to photoablate volumetric portions of an exposed corneal surface, thus modifying the shape of the cornea to refocus the incoming light. Photorefractive keratotomy (PRK), laser in-situ keratomileusis (LASIK), and laser epithelial keratomileusis (LASEK) are examples of photoablative refractive surgeries to correct the optical defects mentioned above.

We can now also accurately measure what are known as higher-order optical aberrations with advanced diagnostic technology such as, e.g., a wavefront sensor. These higher-order aberrations come from defects within the overall optical system of the eye (not just a misshapen corneal surface) and contribute to poor vision quality by reducing acuity and/or contrast sensitivity, causing glare, poor low-light vision, and in other ways. Not surprisingly, device manufacturers and practitioners have responded with techniques, instrumentation and devices, and therapeutic procedures that attempt to correct vision to the theoretical limit of 20/8 (known as supervision) or, practically, to optimize vision quality by eliminating, minimizing, or balancing these aberrations, or otherwise directing their attention to the higher-order defects.

For a variety of known and yet undiscovered reasons, the intended results of customized photoablative refractive surgery and customized lens applications including contacts, inlays, onlays, and IOL", for example, have been elusive. Investigators have focused on the structure and physiology, and sophisticated modeling, of the eye to better understand the dynamics of correcting vision defects. The interested reader is directed to an article by Cynthia Roberts, Ph.D., *The cornea is not apiece of plastic*, Jour. Ref. Surg., 16, pp 407–413 (July/August 2000). Dr. Roberts hypothesized that if the cornea were similar to a homogeneous piece of plastic, a procedure known as radial keratotomy (RK) would not have worked because a biomechanical response to the structure altering incisions would not have occurred. (RK is a surgical procedure designed to correct nearsightedness by flattening the cornea with a series of incisions that resemble the spokes of a wheel). There is an increasing confidence among persons skilled in the art of refractive vision correction that the biomechanics (the biodynamic response of the eye to an invasive stimulus) of the eye, specifically of the cornea, significantly affects the outcomes of laser vision correction. Roberts, id, reports changes in anterior corneal geometry due merely to the keratectomy (flap cut) prior to laser ablation. The biomechanical corneal response to an invasive stimulus such as a keratectomy prior to LASIK or the severing of corneal lamellae by the laser in a PRK procedure can be explained, according to Roberts, by conceiving the cornea not as a piece of plastic, but rather as a series of stacked rubber bands (lamellae) with sponges between each layer (interlamellar spaces filled with extracellular matrix). The rubber bands are hypothesized to be in tension, since there is intraocular pressure pushing on them from underneath, and the ends are held tightly by the limbus. The water content of each sponge depends upon how each rubber band is stretched. Greater tension squeezes more water out of the sponges so the interlamellar spacing decreases; i.e., the cornea gets flatter. Thus the act of laser surgery itself to reshape the cornea may alter the corneal bio-structure with the effect that what you see is not what you get. U.S. Patent Application Publication 2002/0103479A1 to Sarver discusses optimizing the predictability of a vision correction method using surgical outcomes in an iterative analysis to create an optimized treatment outcome. Published PCT application WO 00/45759 discusses the interaction between the photoablative laser system used and the wound healing response of the eye and concludes that correction factors ("fudge factors") in the range of ±1000× must be inserted in the sum of Zernike coefficients and Zernike polynomials to account for the eye's healing response. Published U.S. patent application Ser. No. US 2002/0007176A1 discusses a radially dependent ablation efficiency in the form of a modifying polynomial based on the optical path difference between a plane wave and a measured wavefront from a patient's eye. In many instances, surgeons will modify the manufactures' treatment profiles by their personal nomograms, which typically only provide a power shift correction. This type of personal modification, however, is generally based upon a relatively small sample of patients and procedures, thus general applicability and optimization may not be achieved. U.S. Pat. No. 5,891,131 entitled "Method and Apparatus for Automated Simulation and Design of Corneal Refractive Procedures" describes a computerized finite element method for simulating patient-specific corneal deformation in response to corneal incisions and/or corneal ablation procedures. The patent provides a general framework for this type of approach but does not appear to have solved the problem of optimized predictive analysis. A comprehensive review of finite element methods for simulating refractive surgical procedures on the human cornea is set forth in a 1994 dissertation by Datye which concludes that further work needs to refine the analysis and include other effects and phenomena which may be important in corneal modeling. All of these efforts highlight the attempts by manufacturers and practitioners to modify and customize ablation algorithms or nomograms to more accurately predict and achieve desired refractive outcomes. It is apparent, however, that the puzzle representing perfect vision, supervision, emmetropia, or optimum vision quality, by whatever name, still has missing pieces. For example, induced spherical aberration and other higher-order aberrations are known conventional post-LASIK effects that cause residual vision defects and sub-optimum visual quality. However, the cause and elimination of these treatment induced aberrations continue to challenge manufacturers and practitioners alike.

In view of the aforementioned developments, the inventors have recognized a need for hardware, software, and methods that will facilitate optimum outcomes of therapeutic ophthalmic procedures, in particular, photoablative refractive vision correction and, alternatively, customized ophthalmic optics, that result in optimum vision quality and greater patient satisfaction.

SUMMARY OF THE INVENTION

The instant invention is directed to apparatus and methods that enable predictive outcomes for proposed therapeutic ophthalmic corrections including photoablative refractive surgical procedures and customized ophthalmic optics, and which support a transactional model for providing the predictive outcomes. Reviews of numerous clinical studies to date indicate that no single or simple combination of factors appear to explain the differences between calculated or desired photoablative refractive outcomes and actual outcomes, nor are they outcome predictive. In other words, there is no assurance that the surgical procedure/technique or the ablation algorithm that is used to treat today's myopic patient will produce the same outcome if used on tomorrow's similarly myopic patient. An interesting observation that has been made, however, is that consistency and standardization in all aspects of photoablative refractive surgery produces better therapeutic (corrective) outcomes. Accordingly, the embodiments of the invention involve the use of optimized theoretical and historical, outcome-determinative data to generate a best predictive instruction (e.g., optical zone size, keratectomy depth, an ablation algorithm for driving a therapeutic laser, etc.) for the practitioner's use to optimize the outcome of a proposed vision defect correction. To illustrate, suppose that over the course of 1000 myopic correction procedures a surgeon enters all parameters thought to influence the outcome of the procedure into a statistical analysis program of a computer. These parameters might include, for example, patient profile information (e.g., refraction, biographical, cultural, etc.), practitioner technique (nomograms, historical outcome data, etc.), equipment specifications (e.g., laser make, model and operating parameters, software version, principle of diagnostic examination, etc.), the diagnostic procedure (e.g., aberrometry, elevation based topography, ultrasound, OTC, etc.), the ambient environment conditions (e.g., temperature, humidity, time, etc.), and other factors not listed nor so limited. The computer program can analyze this historical input data to determine, for example, the statistically significant parameters and their relationships to past therapeutic outcome success. For today's patient #1001 with a known myopic defect, the surgeon can enter into the computer, by manual or automatic means, new, prospectively relevant parameters. The computer, in turn, can analyze this information in light of the optimized theoretical and historical information that it has access to, and generate an outcome-predictive instruction, such as a customized laser ablation shot profile algorithm, for example, for driving a therapeutic laser system, that is predictive of an optimized outcome for correction of the measured defect.

In accordance with this illustrative description of the invention, an embodiment of the invention is directed to a system that provides a predictive outcome for a proposed therapeutic ophthalmic correction that includes a collecting and transmitting station (or platform) for receiving a plurality of prospective therapeutic-outcome-influencing information (pre-operative data in the non-limiting case of photoablative surgery) relating at least to either a patient and/or a practitioner and/or a diagnostic measurement and/or a therapeutic condition, and/or an environmental condition, and for transmitting the plurality of information to a computing station. The computing station can receive the plurality of information, store a plurality of historical, therapeutic-outcome information that has been derived from an optimization analysis of theoretical and historical, prospective therapeutic-outcome-influencing information relating at least to either a patient and/or a practitioner and/or a diagnostic measurement, and/or a therapeutic condition, theoretical treatment plan, actual outcomes data, and/or an environmental condition, and then provide an analyzed output that is a best predictive instruction for obtaining an improved therapeutic ophthalmic correction. In an aspect of this embodiment, the collecting and transmitting station could be a computer station that is interfaced by hardware and/or software means to any of a variety of diagnostic devices (e.g., wavefront sensor, topographer, pachymeter, tonometer, etc.), to a therapeutic system (e.g., excimer laser, custom ophthalmic lens platform, etc.), to an operating room "weather station," and/or that provides means for practitioner input of other prospectively relevant new data. In this and other embodiments according to the invention, some or all of the new outcome-influencing information could be collected automatically by the various instrumentation and transmitted to the computing device, or input manually by the practitioner, assistants, or the patient via a keypad or other known means.

In various aspects of the invention, the computing station could be part of a local, inter-office system or, alternatively, it could be a remote server on a network, and/or internet based. Transmissions to and from the computing station could be facilitated by any waveguide-based or wireless means, or by portable media such as a CD or disk. An advantageous routing medium would be secure internet transmission.

The software and data structure for performing the optimization analysis of the theoretical and actual historical therapeutic-outcomes and the analyses of the new information for generating and providing the best predictive instruction can take various approaches. Preferred, but non-limiting examples include statistical analysis (e.g., multiple linear regression), multidimensional vector (matrix) analysis, neural networking, and finite element analysis (FEA). Databases may be composed of, e.g., individual practitioner data, FDA clinical data, pooled third party results with real-time updating, manufacturers' clinical data, etc. Computer stations, network servers, diagnostic devices, therapeutic devices, and interface hardware and software do not in and of themselves constitute parts of the invention per se as they are all independently available components.

Alternatively, an embodiment of the invention is directed to an executable instruction, embodied in a deliverable means to an end user-controlled device, that can be used to provide a predictive outcome for a therapeutic ophthalmic correction.

In another embodiment, the invention is directed to an ophthalmic diagnostic and/or treatment system including diagnostic and/or treatment components, and a graphical user interface (GUI) having a display and a selection device that facilitates the selection of collected information for analysis with optimized historical information provided in or by a data structure, and resulting in an outcome-predictive instruction for a proposed vision correction procedure.

Another embodiment according to the invention describes a method for providing a predictive outcome for a proposed therapeutic ophthalmic correction. The method includes the steps of collecting a plurality of therapeutic-outcome-influencing, "new" information including at least ophthalmic defect information about a patient; providing this new information to a computing platform that contains a data structure including optimized, theoretical and actual historical, therapeutic-outcome information for the determined ophthalmic defect; and generating, via the computing platform, a best predictive instruction for a proposed corrective treatment of the determined ophthalmic defect based upon an analyses of the new therapeutic-outcome-influencing information in conjunction with the historical outcome information. A preferred aspect of this embodiment describes a method for providing a predictive outcome on a fee or transactional basis as a business model.

In all of the embodiments described, the preferable optimization approaches include either statistical analysis, matrix analysis, neural networking, or FEA in combination with the parameters of a corneal ultra structural model (CUSM). The preferable diagnostic station includes an aberrometer such as, for example, the Zywave™ wavefront analyzer and the Orbscan® corneal analyzer (Bausch & Lomb Incorporated, Rochester, N.Y.); the preferable therapeutic station includes a 193 nm, flying spot, excimer laser system such as, for example, the Technolas 217Z™ excimer laser system utilizing the Planoscan® or Zylink™ software platforms (Bausch & Lomb Incorporated, Rochester, N.Y.); the preferable therapeutic procedure is LASIK; and the preferable best predictive instruction is a modified, custom ablation algorithm for driving the laser; however, the invention is not so limited in these regards as described herein.

These and other objects of the present invention will become more readily apparent from the detailed description to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

DETAILED DESCRIPTION OF PREFERRED EMBODIMENTS OF THE INVENTION

Figure 1:
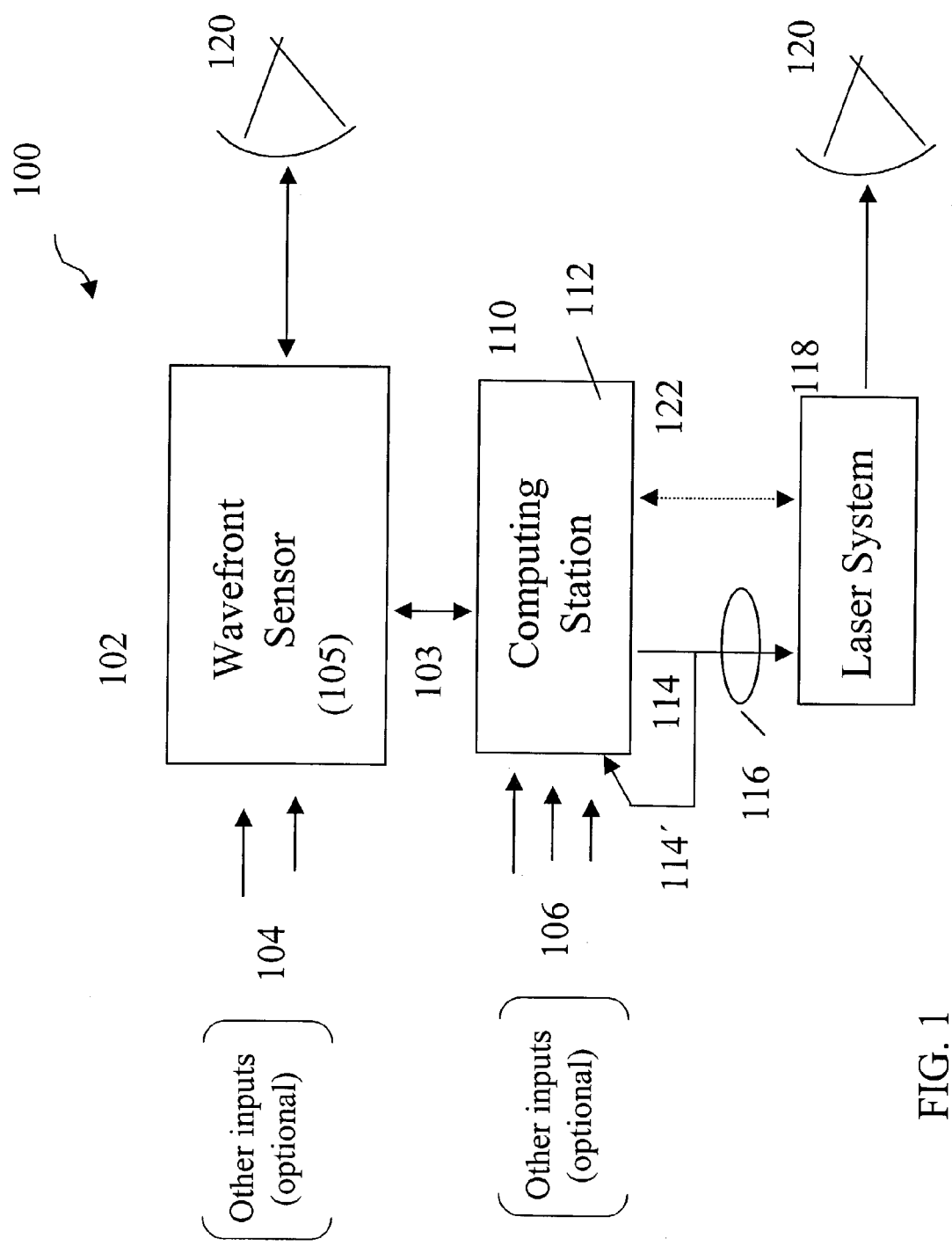
FIG. 1 is a block diagram of a system according to a preferred embodiment of the invention.

FIG. 1 illustrates a system 100 for providing a predictive outcome instruction for a proposed therapeutic ophthalmic correction. The outcome is effected preferably by a customized LASIK treatment to correct lower-order and higher-order aberrations that cause vision defects in the patient's eye 120, or a custom retreatment for a decentered ablation, for example. However, it is to be appreciated that the capture, feedback, and analysis of data does not restrict the invention merely to LASIK; rather, the strategy and implementation of the invention will apply to PRK and LASEK, for example, as well as to the design and performance of custom ophthalmic optics including contact lenses, IOL's, inlays, and onlays. A collecting and transmitting station 102 is shown in the form of a wavefront sensor. The wavefront sensor 102 measures the preoperative optical aberrations of the patient's eye 120, preferably up to the fifth, and in some cases the seventh, Zernike order, or equivalent. An exemplary wavefront sensor, which is not in and of itself a part of the invention per se, is described in Williams et al U.S. Pat. No. 5,777,719, the contents of which are herein incorporated by reference in their entirety to the extent allowed by applicable patent laws and rules. Manifest refraction of the patient's eye can also be obtained from the wavefront sensor data as described, for example, in commonly owned pending U.S. provisional application Ser. No. #60/284,644 filed Apr. 28, 2001. Manifest refraction data and higher-order aberration data represent a subset of prospective therapeutic-outcome-influencing information 105 relating to the patient. The arrows 104 represent other prospective therapeutic-outcome-influencing data relating, for example, to the practitioner, other diagnostic measurements, therapeutic conditions, and/or environmental conditions. Illustratively, the doctor may wish to input personal nomogram information and past outcome data for similar vision defects as currently measured, as well as the make, model, and operating principle information about the wavefront sensor and the laser (therapeutic device) that will be used to correct the patient's vision defect, operating room ambient conditions, or any other information that could prospectively influence the results of the customized photoablative surgery. As a further example, the practitioner may want to optimize post-surgical spherical (and others) aberration to improve low-light vision quality and, therefore, would include preoperative spherical aberration as a specific input parameter.

All of this information 105 (104) is manually or automatically input to, or collected by, the collecting and transmitting platform 102, and transmitted as shown at 103 as "new" information to a computing station 110. Transmission 103 can occur by known means including, but not limited to, directly, via the internet, telephonic data transmission, wireless communication, via CD, disk, etc. As such, the computing station 110 can be located locally, in the doctor's suite, for example, or remotely. In any case, the computing station may be capable of receiving new or historical input from other sources as indicated by the arrows 106, and described in more detail below.

The computing station 110 preferably operates in three functional capacities. One of these capacities is to receive "new," prospective therapeutic-outcome-influencing information 105 as described above. In a second capacity, the computing station includes a storage medium, e.g., disk space, and an appropriate data structure (described below), that contains and/or can generate optimized theoretical and actual historical, therapeutic-outcome information 112. This historical information has been derived from optimization analyses of actual historical data, prospective therapeutic-outcome-influencing information, and theoretical surgical plans relating to patients, practitioners, diagnostics, therapeutics, environmental conditions, and so on. For example, a practitioner may have performed 1000 prior LASIK procedures. Each procedure to correct a patient's measured vision defects involved a particular diagnostic measurement obtained with the aid of a particular diagnostic device, a specific laser system with an ablation profile-driving algorithm possibly modified by the surgeon's personal nomogram, and a particular keratectomy procedure for flap creation (LASIK). Each patient had a profile indicating age, race, gender, etc. Ambient operating room conditions provided an environment in which each procedure was performed. And each therapeutic procedure was characterized by an outcome (post-operative results over measured follow-up periods) that was knowingly or prospectively influenced by some or all of the foregoing variables, and perhaps others. By performing analyses of new input data in conjunction with the optimized historical data and prior optimized instructions for a proposed therapeutic procedure (theoretical surgical plan), outcome predictive therapeutic relationships can be determined. When "new" information relating to the $1001^{st}$ procedure is provided for analysis in conjunction with the stored, historical outcome information 112, 114', the computing station 110 can operate in its third functional capacity to output (shown at 114) to the practitioner (or to the laser system) 118 a best predictive instruction 116 for facilitating an optimized correction of the patient's ophthalmic defect. This best predictive instruction preferably is a customized algorithm used to drive the photoablative equipment and procedure, but may include other optimized information relevant to the procedure, such as, e.g., LASIK flap thickness and/or optical zone size.

Figure 5:
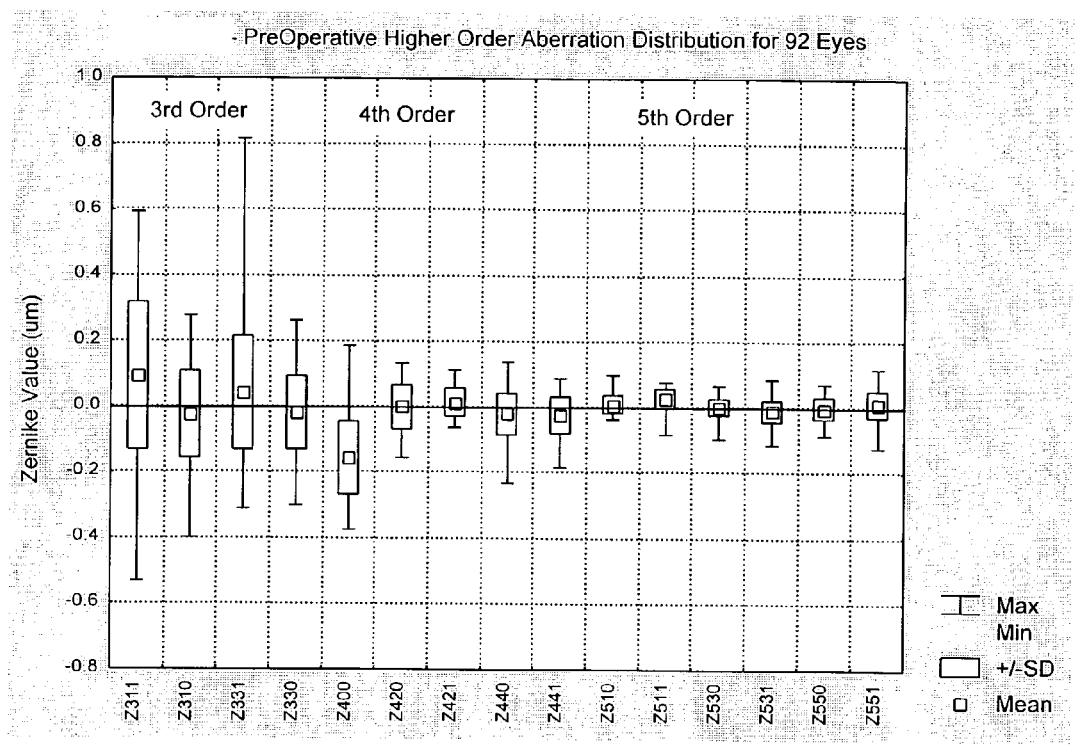
FIG. 5 is a chart showing the distribution of preoperative higher-order ($3^{rd}$, $4^{th}$ and $5^{th}$ Zernike order) aberrations for a clinical study group of 92 eyes.
Figure 6:
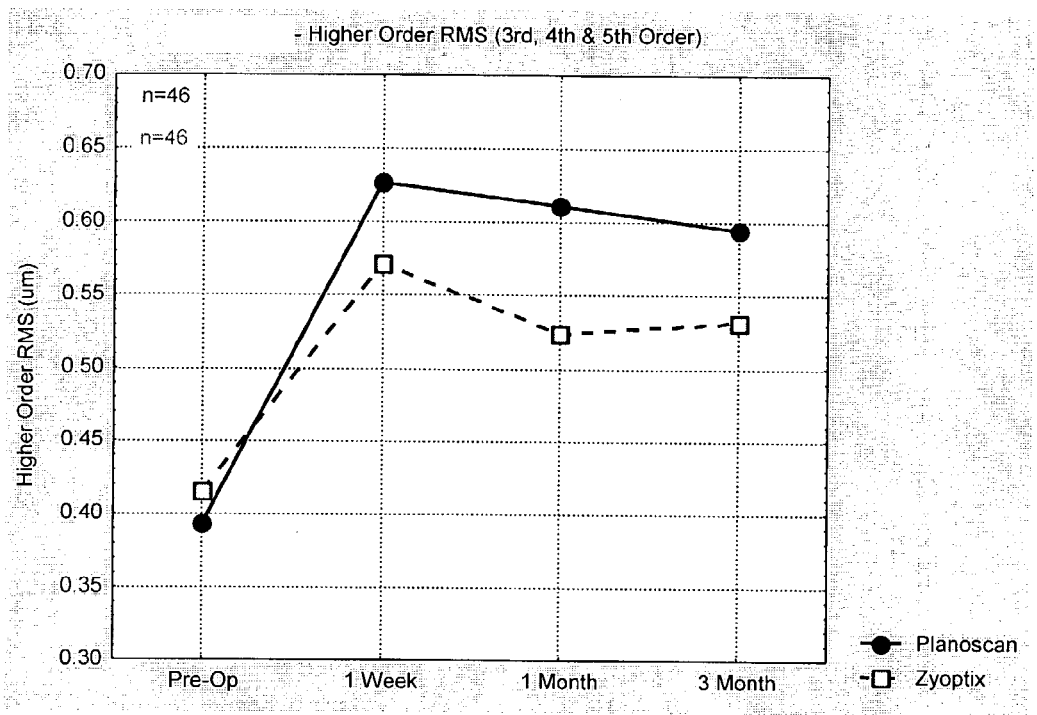
FIG. 6 is a graph showing the RMS magnitude of LASIK-induced higher-order aberrations over time.
Figure 7:
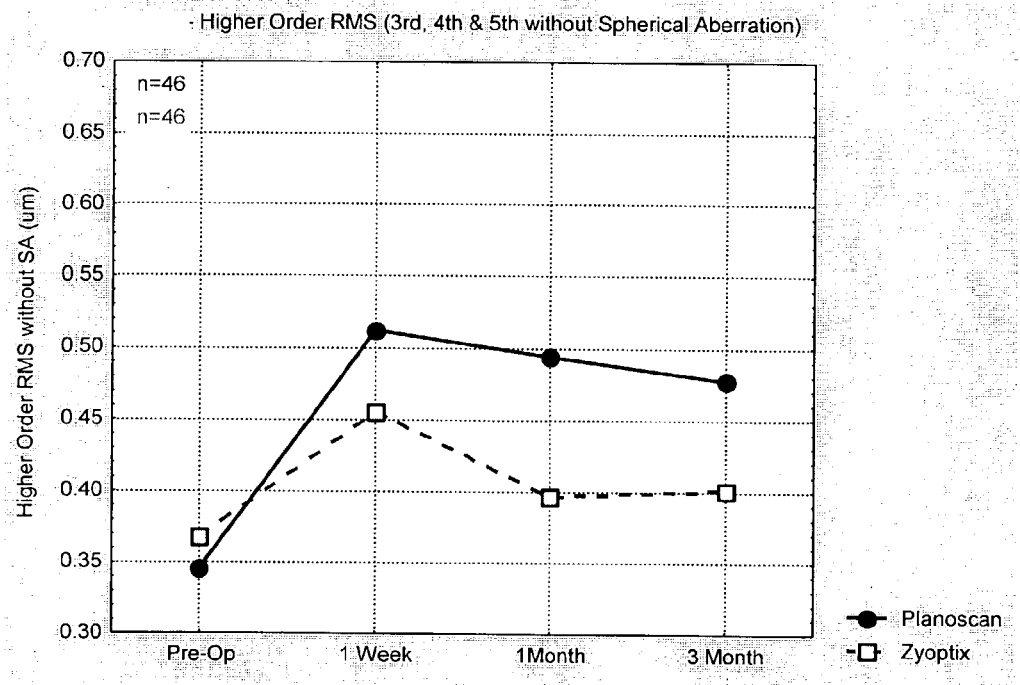
FIG. 7 is a graph showing the RMS magnitude of LASIK-induced higher-order aberrations, but without spherical aberration, over time.

The approach for generating the best predictive instruction 116 according to the invention include various preferred embodiments. A first embodiment utilizes multiple linear regression, for example, to provide a statistical analysis of the actual and theoretical historical outcome data 112, 114' that can then be used in conjunction with the new input data 104, 105. The basis of this embodiment is illustrated as follows with reference to FIGS. 5–9. FIG. 5 shows the distribution of what are referred to herein as higher-order aberrations ($3^{rd}$, $4^{th}$ and $5^{th}$ order Zernike) among 92 pre-operative eyes from a clinical study sample group. As shown, $3^{rd}$ order aberrations ($Z_{3xy}$) represent the majority of preoperative wavefront aberrations in the normal population, with (negative) spherical aberration ($Z_{400}$) also being significant. One known effect of conventional LASIK treatment is the inducement of higher-order aberrations, particularly spherical aberration, which may account for reduced vision quality under low light conditions. FIG. 6 shows measured (RMS) higher-order aberrations preoperatively and at three one-month postoperative intervals for 46 eyes that had Planoscan® (Bausch & Lomb Incorporated, Rochester, N.Y., USA) LASIK treatment, and 46 eyes that had Zyoptix® (Bausch & Lomb Incorporated, Rochester, N.Y., USA) LASIK treatment. Planoscan refers to a conventional (defocus, astigmatism) LASIK treatment algorithm; Zyoptix refers to a custom LASIK treatment algorithm that in conjunction with the Zylink® (Bausch & Lomb Incorporated, Rochester, N.Y., USA) software platform is designed to correct measured preoperative wavefront aberrations. FIG. 7 is a graph similar to that of FIG. 6 except that the spherical aberration term ($Z_{400}$) has been removed in order to show the contribution only by the other $3^{rd}$, $4^{th}$ and $5^{th}$ order Zernike terms.

Figure 8:
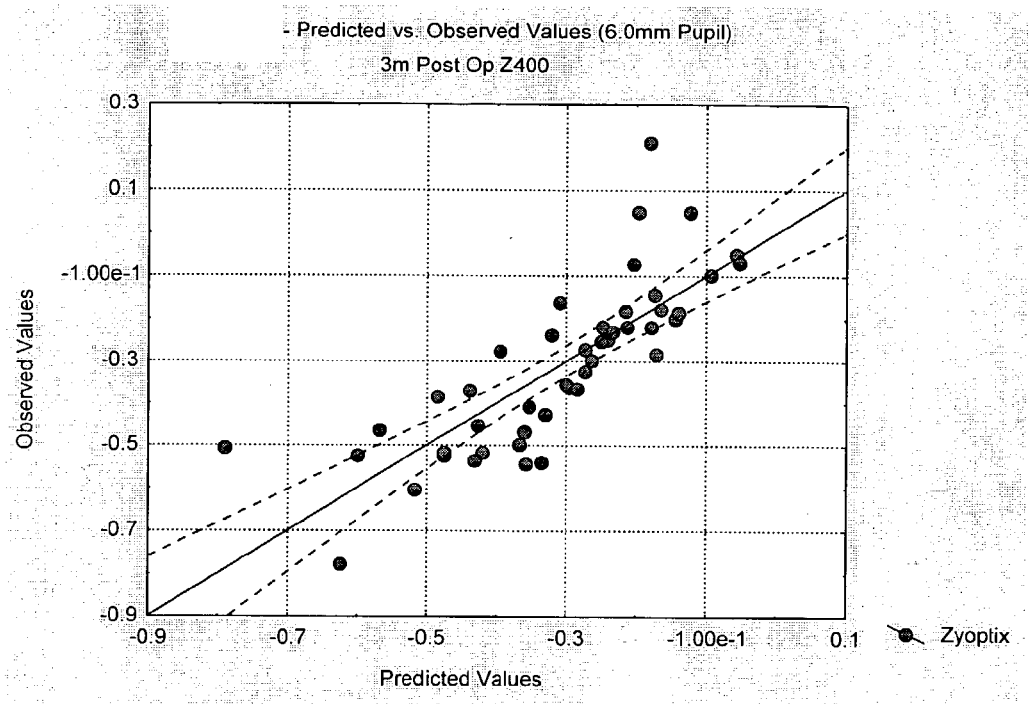
FIG. 8 is a graph based on a linear regression analysis showing predicted vs observed values of post-LASIK spherical aberration according to an embodiment of the invention.
Figure 9:
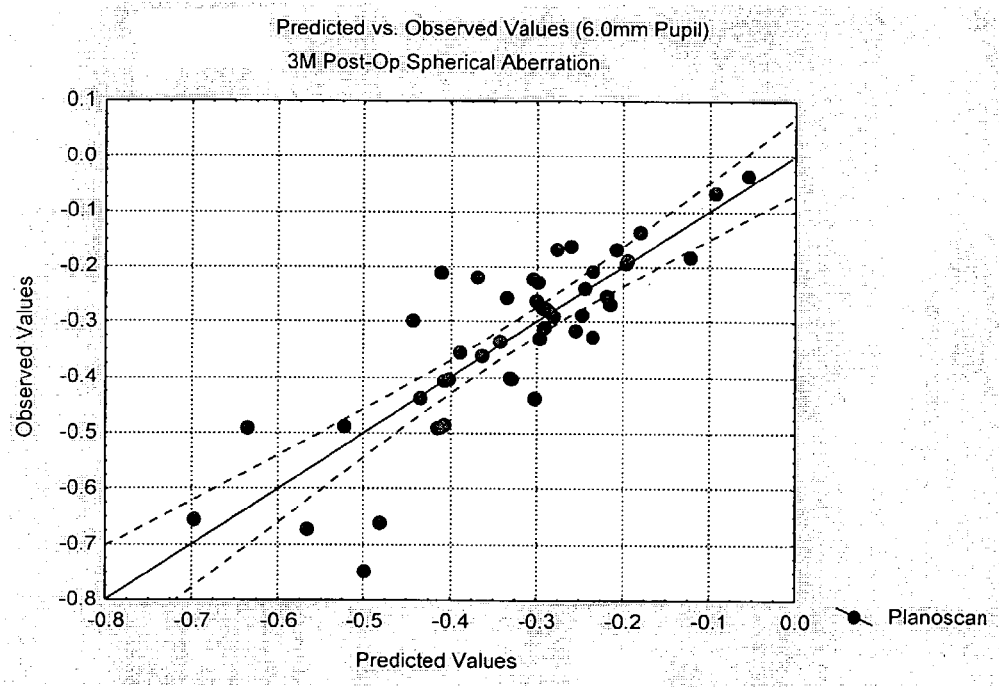
FIG. 9 is a graph based on a linear regression analysis showing predicted vs observed values of post-LASIK spherical aberration according to an embodiment of the invention.

A stepwise multiple linear regression was performed using all preoperative $3^{rd}$ and $4^{th}$ order Zernike coefficients to investigate the predictive nature of the relationship between postoperative spherical aberration and preoperative measures; specifically, to predict the three-month spherical aberration ($Z_{400}$) for the Zyoptix and Planoscan treated eyes at three different pupil sizes, 5.0 mm, 6.0 mm, 7.0 mm. For Zyoptix treated eyes and 5.0 mm pupils (n=51) the relationship $$3\text{Month } Z_{400}=\text{PreOp}Z_{400}*0.387686+\text{PreOp}Z_{200}*0.034882+0.023291$$

gave a correlation co-efficient of r=0.75. For Zyoptix treated eyes and 6.0 mm pupils (n=46) the relationship $$3\text{Month } Z_{400}=\text{PreOp}Z_{400}*0.501336+\text{PreOp}Z_{200}*0.052621+0.042704$$

gave a correlation co-efficient of r=0.80. For Zyoptix treated eyes and 7.0 mm pupils (n=23) the relationship 3Month $Z_{400}$=PreOp$Z_{400}$*0.356462+Pre-Op$Z_{200}$*0.070921+0.068812 gave a correlation co-efficient of r=0.72. As FIG. 8 shows for the 6.0 mm pupil, there is strong agreement between the observed and predicted values using this equation. For Planoscan treated eyes, 5.0 mm pupil, n=52, the relationship 3Month $Z_{400}$=PreOp$Z_{400}$*0.933579+Pre-Op$Z_{200}$*0.023760+0.004549 gave a correlation co-efficient of r=0.84. For Planoscan treated eyes, 6.0 mm pupil, n=46, the relationship 3Month $Z_{400}$=PreOp$Z_{400}$*0.745150+Pre-Op$Z_{200}$*0.037653−0.020633 gave a correlation co-efficient of r=0.84. For Planoscan treated eyes, 7.0 mm pupil, n=23, the relationship 3Month $Z_{400}$=PreOp$Z_{400}$*0.638732+Pre-Op$Z_{200}$*0.055682−0.069077 gave a correlation co-efficient of r=0.81. As FIG. 9 shows for the 6.0 mm pupil data using this equation, there is strong agreement between the observed and predicted values. Thus, "new" information (preoperative spherical aberration) was analyzed in conjunction with statistically analyzed "historical" information (pupil size, postoperative spherical aberration, defocus) to generate a predictive instruction for optimizing a patient's three-month postoperative spherical aberration.

According to another embodiment, a multi-variable matrix approach could be used to provide the best predictive instruction. The current procedure for determining an ablation profile based upon a thin lens formula is limited by various shortcomings. For instance, biodynamics and healing response are not considered, and simple use of the Munnerlyn formula leads to a tissue removal profile based only on refractive power changes. Moreover, the current linear approach does not adjust for individual procedure differences among surgeons. What results from all of this is refractive power adjustment through personalized nomograms without viable means to effect aberration correction adjustment.

Illustratively, let Z be a vector representing a Zernike vector output from an aberrometer related to the corneal surface to be removed.

$$Z = (n-1) \begin{pmatrix} Z_1 \\ Z_2 \\ Z_3 \\ \vdots \\ Z_n \end{pmatrix}$$

where the wavefront data output from the aberrometer has been modified by the index of refraction, n, of the cornea. Define M' as a clinical matrix having terms that describe the interdependence of various Zernike terms as affected by wavefront and non-wavefront information such as, e.g., topography or other preoperative patient data. For example, M' could be a diagonal matrix $$M' = \begin{pmatrix} C_{11} & & & & \\ & C_{22} & & & \\ & & C_{33} & & \\ & & & \ddots & \\ & & & & C_{nm} \end{pmatrix}$$

where the matrix elements $C_{ij}$ are terms resulting from a multiple linear regression of preoperative and postoperative spherical aberration measurements as described above. As interdependencies between various Zernike terms are further realized, typically through clinical studies, M' will fill out as a full n×m matrix. Another matrix, M", can be generated from actual and theoretical historical outcome information. In form, $$M'' = \begin{pmatrix} H_{11} & H_{12} & \cdots & H_{1n} \\ H_{21} & H_{22} & \cdots & H_{2n} \\ \vdots & & & \\ & & & H_{mn} \end{pmatrix}$$

Preferably, M" would be developed with the same analysis software used for M', to develop a feedback loop to regularly update M" to reflect the surgical procedure. A resultant matrix Z'=M"×M'×Z+(constant) represents information for generating an optimized, predictive instruction for correcting the patient's vision defect. In a broadened aspect of this embodiment, M" may contain information from a plurality of sources and thus act as a central database for providing predictive instructions to any surgeon wishing to utilize a service providing such information. In this case, M" could be updated as new outcome information becomes available. Update information could be obtained from multiple sources through a variety of acquisition schemes including purchase or lease of the relevant information.

Figure 11:
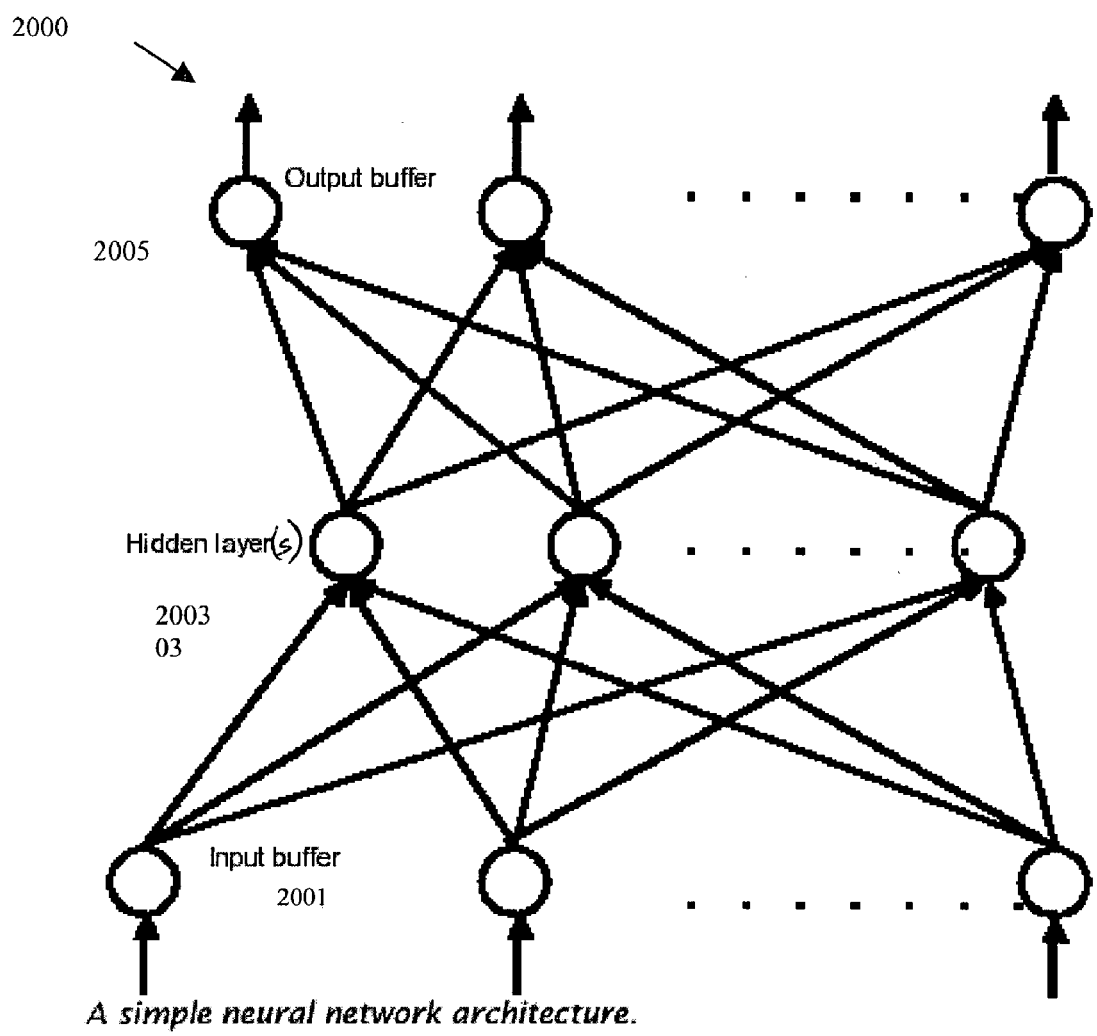
FIG. 11 is a schematic of a simple neural computing model involving data based training.

In a different embodiment according to the invention described with reference to FIG. 11, a neural networking environment 2000 is an approach that could provide the best predictive instruction to the surgeon. Neural networking, sometimes referred to as neuro-computing, is a fundamentally new approach to information processing, and is the first viable alternative to sequential programmed computing. Neural networks offer distinct advantages for applications where there is little or no existing knowledge of how to develop an algorithm. Neural networks can operate where there is imprecise or ambiguous data, and can be trained to produce reliable predictions from historical information. A neural network can adapt to external input by modifying memorized data according to specific learning laws. These in turn may re-size the shape of the network (number of connections) as it maps the problem. Often there are large numbers of solutions to any problem but the advantage of a neural network approach comes from the network learning to produce the optimum solution or result. In accordance with an embodiment of the invention, the task of improving refractive surgical outcomes can be viewed as the analysis of a large and varied set of patient, diagnostic and historical data and the prediction of ablation algorithms that give the desired outcome. Since much of the data provided for determining ablation algorithms has proven to be difficult to analyze and determine correlation coefficients by traditional statistical methods, neural computing may prove to be an ideal tool for analyzing a broad base of diagnostic data and providing optimized, predictable outcomes. The neural network may function in a back-propagation mode as follows in FIG. 11, which illustrates a simple neural computing model 2000 involving data based training. All relevant pre-op data that may be applicable to the outcome of the procedure (prospective outcome-influencing information) is input to the buffer layer 2001. The hidden layer 2003 may consist of the historical information (rules and relationships) that would be proprietary to a third party, which allows the system to test and learn from existing data and outcomes. Knowing historical outcomes from past procedures, the hidden (analysis) layer 2003 is trained to perform appropriate calculations to achieve desired outcomes by pre-assigning known weighting factors to generate intermediate outcomes. As new patient data, theoretical outcome data, and actual outcome data become available, the hidden layer 2003 continues to be trained to output a best predictive instruction at the output buffer 2005.

Figure 12:
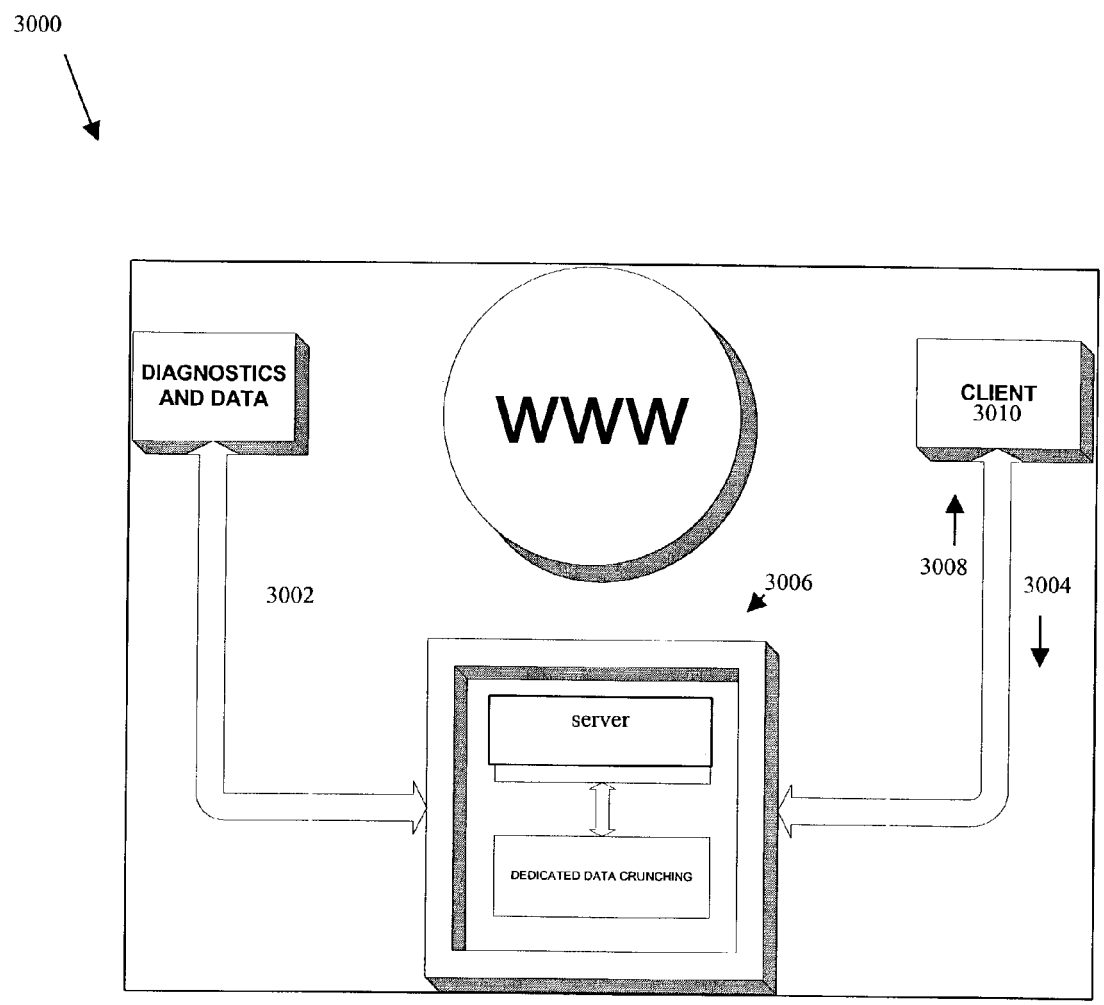
FIG. 12 is a diagram showing implementation of web based model for outcomes analysis and ablation pattern determination.
Figure 13:
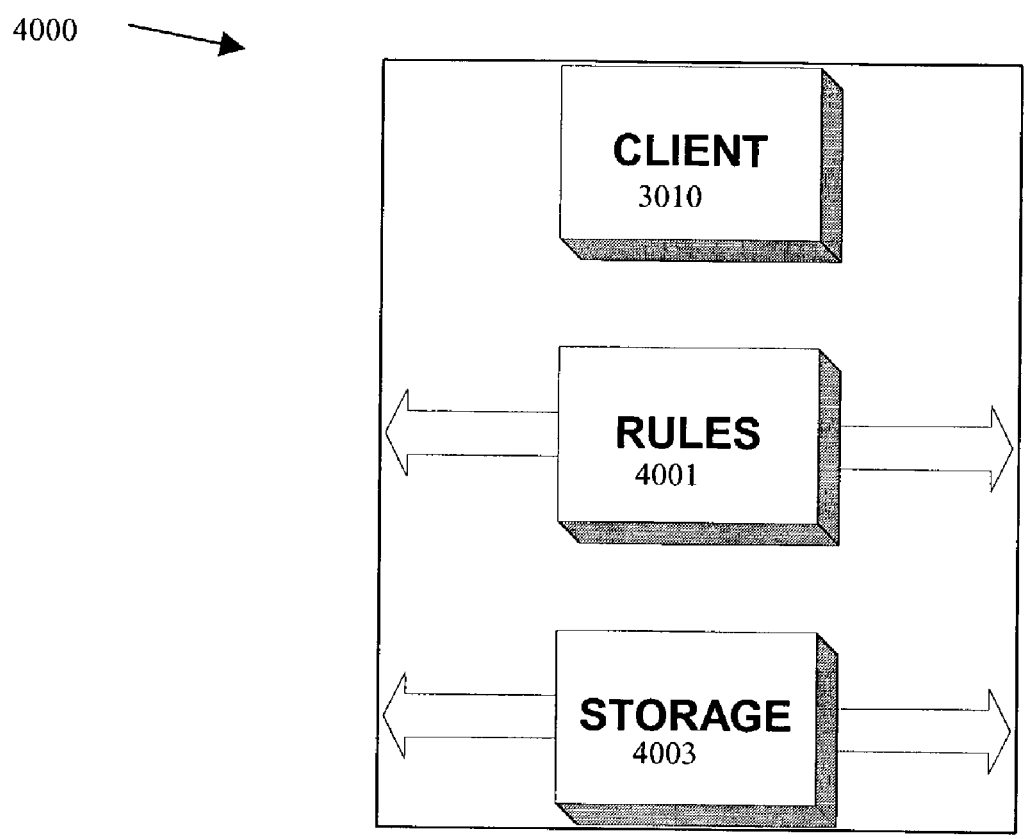
FIG. 13 is block diagram of an architecture for business model according to an embodiment of the invention.

The unique property of neural networks is that they can be trained from an existing set of data and known solutions to update the hidden layer weighting functions and rules to improve outcomes from future information. The larger the database of known outcomes the more effective the network becomes at producing optimal solutions. The neural computing model would preferably be implemented on web-based application models 3000, 4000 as shown in FIGS. 12 and 13, respectively. All information 3002, 3004 would be collected at a computing site 3006 where data analysis could be completed and predictive best-instruction output 3008 returned to the client 3010. Input and output would preferably be through a web-based application that interfaces with a computing architecture 4000 shown in FIG. 13. The rules box 4001 refers to the necessary computer software and analysis techniques to complete the process. The storage requirements 4003 also could be defined. Once the system was defined it could be expanded easily to support a client base of any size. This represents a standard scalable architecture for web-based businesses.

A fourth approach embodied by the invention relies on a probabilistic finite element analysis (FEA) using accurate corneal ultra structural model (CUSM) input and a correct finite element in conjunction with new input data as described above to obtain Young's Modulus data and Poisson's Ratio information about the eye. It has been proposed that a proper biodynamic model of the eye must include both a structural modeling of the cornea provided by an ultra structural fiber model and a fluid dynamic analysis based upon a hydrated matrix model component. These two aspects of the corneal system, referred to herein as the Cornea Ultra Structural Model (CUSM), are outlined as follows.

Biologic tissues, when examined on a macroscopic scale, appear non-isotropic and highly nonlinear. However, tensile tests that measure this behavior do not reproduce a valid physiologic environment. For example, elongating strips of corneal material at first produces no measurable tension, but instead, a release of water. Eventually, often at hyperphysiologic conditions, tension rises exponentially over a limited range. These complex nonlinearities may, however, be the result of ignoring mechanisms that are for the most part linear, but complexly intertwined. Nevertheless, as a linear composite of linear mechanisms retains its linearity, there must be some essential nonlinearity. Ideally, this nonlinearity is fundamentally simple, and is magnified by the complexity of the overall, mostly linear, mechanism. If this is the case, an accurately predictive and widely applicable model will only be realized after the essentials of all ultra-structural mechanisms are fully incorporated.

Figure 14:
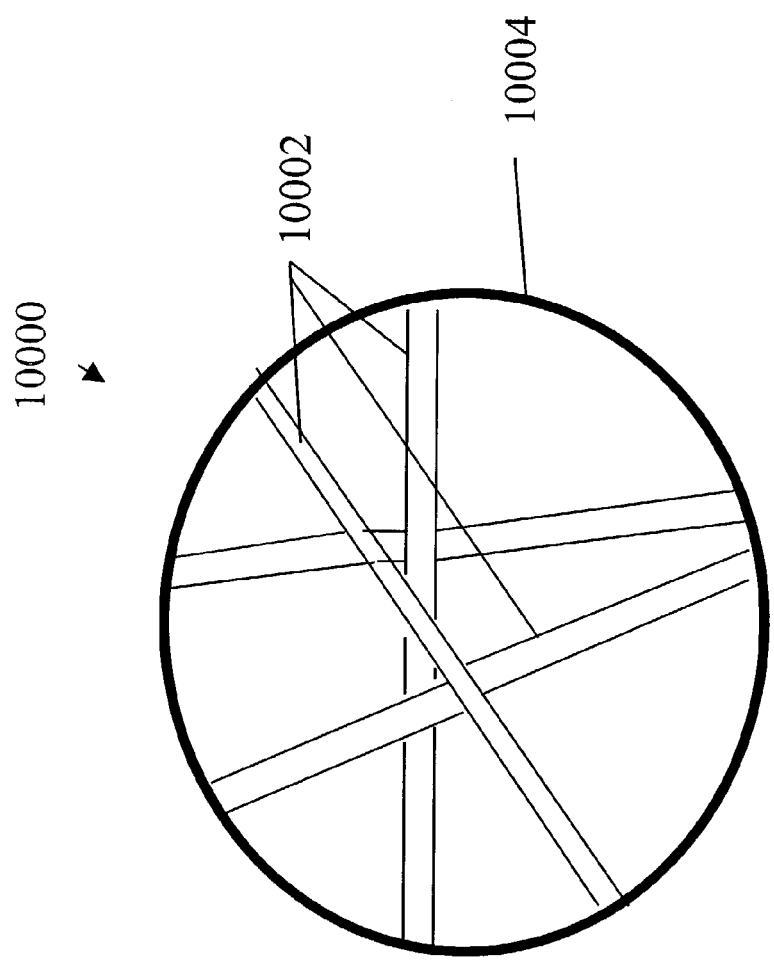
FIG. 14 is a schematic illustration of overlaying fibril layers of a cornea.

Ultra-structurally, the cornea is a complex composite material consisting of oriented fibers (lamellae) 10002, as shown diagrammatically in FIG. 14, primarily arranged in layers, spaced by a hydrophilic matrix of glycosaminoglycans (GAGs), and filled with water, some bound and some free. An accurate modeling tool, therefore, must include or explain the following facts:

1. Members under stress are not shells, but layers of fibrils. Intraocular pressure (IOP) puts fibrils under tension. This tension is distributed uniformly throughout the corneal thickness (i.e., anterior fibrils and posterior fibrils are for the most part equally stressed).
2. Overlaying fibril layers are crossed (near perpendicular). Human corneas have specific directions of fibril predominance (both horizontal and vertical). This directivity, and other geometric factors like the rate of peripheral increase of pachymetry, varies with species. Thickness abnormalities (e.g., nasal thin spots) arise from fibril layer nonuniformities and are developmental in nature.
3. Relatively larger circumferential stresses at the limbal junction (where an 8 mm radius surface joins a 12 mm radius surface) are supported by a circumferential fiber ring 10004.
4. Scleral fibers are crossed rather than being organized into extensive parallel-fibril layers. Minimum scleral thickness occurs at its equator (with respect to the optical or symmetry axis of the eye).
5. Surface shape is determined by fibril lengths and stabilized by layer interconnections. Normal (i.e., healthy and not post-surgical) shape is unaffected by significant changes in intraocular pressure. Under these modest stresses, fibrils do not extend appreciably.
6. Surface shape changes occur when fibrils are cut, redistributing the stresses non-uniformly and allowing unloaded fiber layers to expand. The expansion is determined by a complicated interaction of fibril and cross-link stresses with the inter-fibril matrix pressures. See Roberts, id
7. Fibril spacing necessary for transparency is precisely maintained. This necessitates the observed stromal structure as numerous layers of tiled fibers (a fiber being a compact group of parallel fibrils).
8. Increasing peripheral opacity of the cornea, especially near the limbus, is indicative of less fibril organization (e.g., an increase in fibril crossings) near the limbus.
9. Fibril spacing is maintained by a complex balance between springy spacing materials (the interfibril GAGs) and fluid pressure (which at homeostasis is relatively negative, about −60 mmHg). The negative pressure or suction (imbibition) is maintained by the endothelium.
10. Over the physiologic range, corneal thickness is proportional to hydration. Excised stroma in saline expands up to 150 percent its physiologic value on a time scale of hours. When constrained in saline, a substantial positive swelling pressure can be measured. When suction is applied to counteract the swelling pressure, a negative imbibition pressure can be measured.
11. Swelling and imbibition matrix pressures are larger in magnitude than the intraocular pressures responsible for generating the fiber tension. Hence, interfibril matrix pressures can never be ignored.
12. Inter-fibril cross-links, the matrix composition, the fibril layer structure, and fibril orientation are all spatially dependent within the cornea. Local fiber layer orientation is at least partially responsible for observed non-uniform meridional strains induced by excess intraocular pressure.

13. The cornea is flaccid in youth, becoming more rigid with age. This is presumably due to increased cross-linking and/or stiffening (through accumulation of various molecular species) of the inter-fibril matrix with age.

Corneal Fiber Model

For the purpose of explaining the invention, fibers are theoretically defined as compact groups of fibrils. Thus the fiber is a modeling construct rather than physiologic entity. It is a way of subdividing a physiologic layer. The corneal fiber model follows from three postulates:

1. Fibers follow geodesics. Corneal fibers can not withstand bending moments, and therefore, they are for the most part under pure tension. A fiber under pure tension follows a straight line, which when confined to some surface, is a geodesic of the surface (e.g., a great circle of a sphere).
2. Fibers tile the surface. Every layer is an individual tiling of fibers. Gaps created by crossovers would generate significant optical scatter and therefore are avoided.
3. Fiber area is conserved. The number of discrete fibrils and fibril spacing is conserved. Therefore, as a fiber is defined by the distinct fibrils it contains, fiber area must be conserved.

Figure 15:
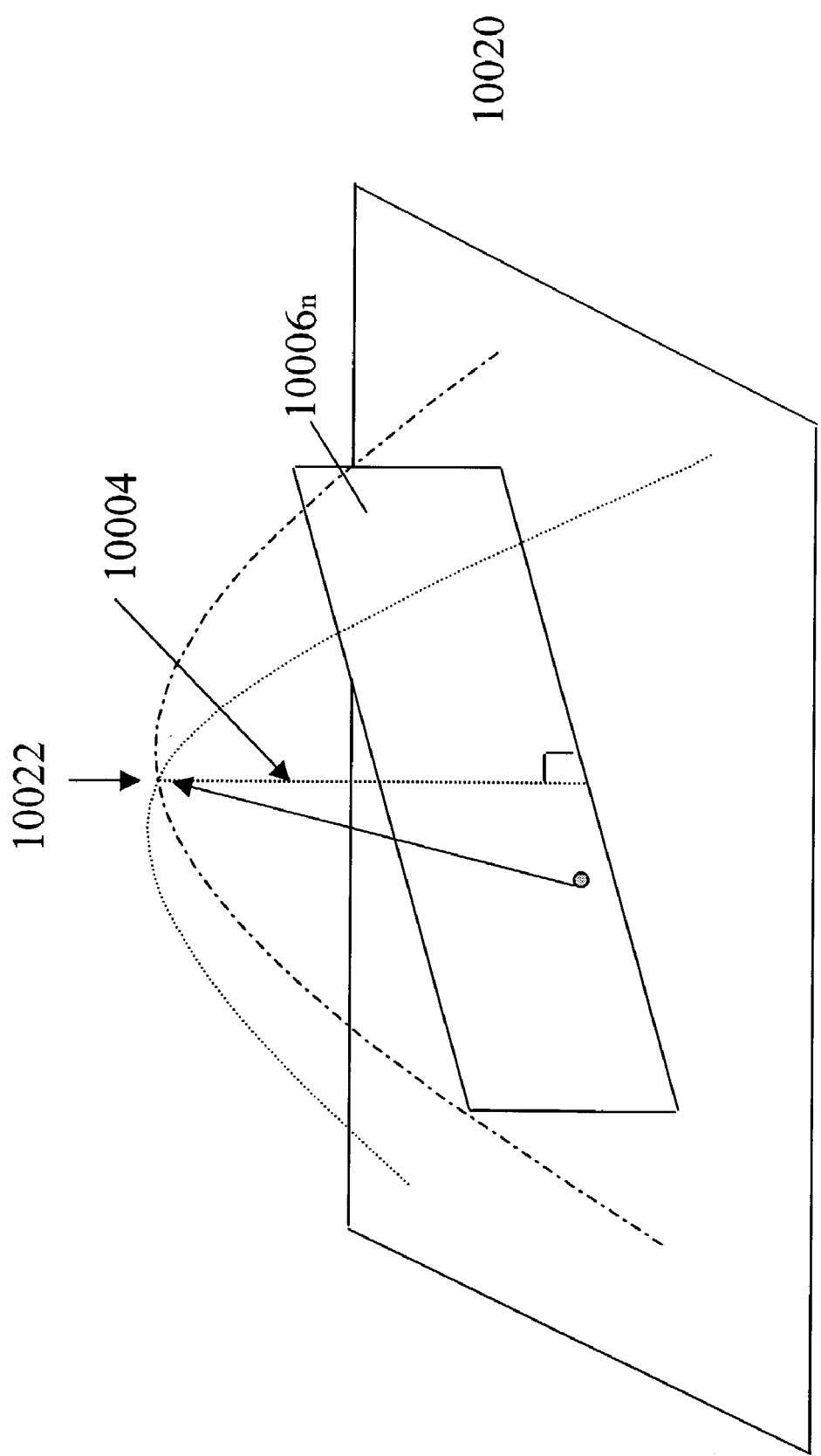
FIG. 15 is a schematic illustration of definitional terms used in the description of the invention.

The following terminology, with reference to FIG. 15, will aid the reader in understanding the corneal fiber model according to the invention. The limbal plane 10020 is a plane that best fits the limbus. The corneal apex 10022 is the central anterior surface point farthest from the limbal plane. The corneal axis 10004 is the normal to the limbal plane that intersects the corneal apex. Meridional planes $10006_n$ contain the corneal axis. The central fiber in any layer is the one that intersects the corneal axis. Layer fibers farthest from the central fiber are lateral fibers. For any layer, the medial plane is the meridional plane that perpendicularly intersects the central fiber.

The following consequences can be immediately deduced from the model postulates:

1. Fiber aspect ratio changes gradually from medial to peripheral locations. If the area of a fiber is conserved and if fibers always follow geodesics, then a fiber laid over a convex surface must be thinnest medially, increasing peripherally. This explains in part why stromal thickness increases peripherally. However, the inventors postulate that the observed increase in thickness is not fully explained by individual fiber aspect changes. To reproduce the normal human thickness distribution, different fibers in the same layer must have different areas, the area increasing from the central to lateral fibers.
2. Lateral fibers blend naturally into the limbal circumferential fiber ring. Geodesic orientation causes lateral fibers to bend towards the periphery. The most lateral fibers therefore flow easily into the limbal fiber ring.
3. Corneal organization (tiling) leads to scleral disorganization (crossing). Tiling fibers in a single layer follow geodesics that over a sphere would cause all the fibrils to cross at two opposing diametrical points. Taking this spherical example a step further, the multiplicity of overlaying layers crossing at all angles together contain fibrils that all cross at the equator, the locus of the crossing diametrical points. Topologically this means that the uniform tiling over the cornea necessarily leads to extensive fibril crossing in the annular limbal region.

How is corneal shape determined? If fibers are formed under tension, then a flat surface might be expected. However, it has long been observed that the developing cornea must be pressurized to form properly. Its final shape may be determined by the initial arrangement of the ectodermal cells responsible for generating the stromal fibrils. Pressure bulges this cell layer into a dome. As fibers are laid down they follow the cell layer. Eventually the fiber layer is sufficiently thick and sealed (via linking GAGs) so that the layer can withstand pressure on its own. This puts the fibers under tension and forms a surface with a shape maintained by the already fixed fibril lengths. Repeated layers are added to the surface with the fibrils following the surface geodesics.

Fibers do not follow geodesics outside the cornea. Limbal ring fibers, for example, do not follow geodesics. Also, there is no scleral thickening at its posterior pole, which would be a consequence of minimum equatorial thickness if geodesics were followed. So what is the difference between the cornea and scleral lay-up? The parallel lay of corneal fibers does not permit lateral fiber-bending forces. Hence corneal fibers must follow geodesics. Scleral fibers, being interwoven, can exert lateral forces on one another and follow non-geodesic curves.

Corneal fibrils are conserved. This can be deduced from the repeated observation that fibrils do not seem to end but appear to span the cornea from limbus to limbus (and beyond). If fibril ends are infrequent or terminate in some confluence with another fiber, they would be very difficult to detect. Fibril conservation may not be rigorously correct as it is difficult to envision how any unending fibril could be constructed.

Hydrated Matrix Model

Corneal fibers are bent by an internal pressure gradient set up by the intraocular pressure. For example, if the layer surface were spherical, then the pressure gradient normal to the surface would be given by $$\frac{dp}{dz} = \frac{2\sigma}{R}$$

where p is the intraocular pressure, $\sigma$ is the membrane stress, and R is the membrane radius. It is well known that the fibers are nearly equally stressed and the layer radius is nearly uniform through the corneal depth. Thus the pressure gradient will be nearly constant through the cornea. However, this mechanically-induced pressure gradient is only part of the picture. Hydraulic pressure (actually suction) within the cornea is responsible for governing the inter-fibril spacing. Any accurate prediction of corneal shape must include both mechanisms, i.e., fibril bending due to pressure gradients and inter-fibril spacing due to hydration balance.

The glycosaminoglycan matrix, which maintains the inter-fibril spacing, is very hydrophilic. Imbibed water causes the matrix to expand, and thus fibril spacing is governed by controlling corneal hydration. The physiologically normal state is relatively dehydrated, which requires a negative internal pressure for homeostasis. Thus the mechanical picture of the matrix is one of a springy material under compression brought about by relatively negative hydraulic pressure. The "spring constant" of the matrix can be deduced from measurements of the imbibition or swelling pressure. "Imbibition" is the negative hydraulic pressure within the matrix. "Swelling" is the positive reaction pressure of the compressed matrix. The measured form of the positive swelling pressure, $\Sigma$, can be expressed as $$\Sigma = \Sigma(H) = \Sigma_0 \exp(-c_1 H + c_2 H^2).$$

Although this is expressed mechanically, one should remember that the matrix spring force is driven by imbibition, that is, the bonding of water molecules with the hydrophilic GAGs. Therefore, it is also temperature dependent, $\Sigma$ decreasing with increasing temperature. Hydration, H, is defined as the water mass divided by the dry mass of the cornea (both fibrils and matrix). The swelling pressure relation above is valid over H ranging from 1 to 10. It has been observed that corneal thickness, T, is linearly related to hydration, dT/dH equaling 0.14 mm/H for human corneas.

$$T = T(H) = T_D\left(1 + \frac{\rho_w}{\rho_D}H\right).$$

The dry mass density of the cornea, $\rho_D$, is substantially the same for all mammalian species.

| Description | Parameter value | Measured | Reference |
|---|---|---|---|
| Normal hydration | H = 3.7 | wet and dry mass | |
| Swelling pressure | $\Sigma_0$ = 905.3 Torr | imbibition pressure | Hara (1972) |
| | $c_1$ = 0.8469 | | |
| | $c_2$ = 0.0295 | | |
| Dry mass density | $\rho_D$ = 1.41 ± 0.09 g/cc | mass density | Hedbys (1966) |
| Water mass density | $\rho_w$ = 1.0 | | |

These two hydrated matrix equations, $\Sigma(H)$ and $T(H)$, coupled with the complex fiber mechanics, are sufficient to construct a static model of the cornea.

Figure 16:
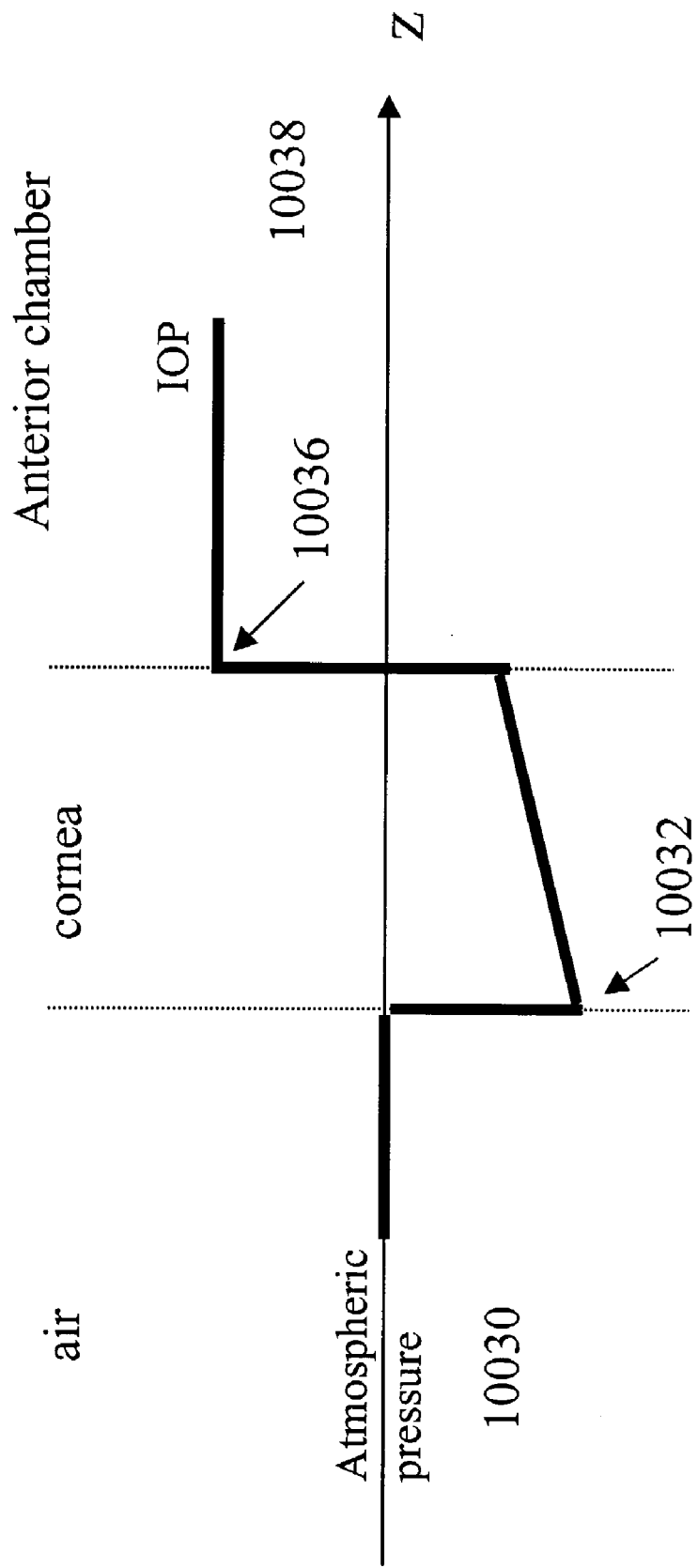
FIG. 16 is a graphical chart of pressures affecting the eye.

The schematic in FIG. 16 shows the normal static hydraulic pressure profile in the human eye from exterior to interior. Starting with atmospheric pressure in the air 10030, there is a negative jump of about 60 Torr to the imbibition pressure 10032. This rapid drop is impressed across the epithelium. Over the corneal stroma 10034 there is a gradual pressure increase, equaling the IOP in total. Across the endothelium 10036 there is a positive jump to the IOP, which is uniform in the anterior chamber 10038. This homeostatic picture, however, will be altered by surgery and other interventions. For example, a study [Odenthal, 1999] examining the effects of a two-hour hypoxic stress noted an overshoot in corneal thickness followed by an exponential relaxation indicative of a damped oscillation. Thus, the required dissipative and capacitive elements do not appear in the static equations presented so far. The missing piece thus must account for the diffusive movement of water within the cornea. A series of diffusion models could be combined with the existing hydration equations to obtain a transport equation, H(x, y, z, t), for $H_2O$ in the cornea. Examples of diffusion models include simple diffusion and chemotactic diffusion (chemical diffusion).

To make accurate biomechanical predictions, corneas must be measured and modeled both generally and individually. Thus, a proper finite element model (FEM) will incorporate what is currently believed by the inventors to be the essential components taken from the CUSM, consisting of (a) fibril orientation; (b) lamellar size and structure; (c) lamellar mechanical properties; (d) hydration transport mechanisms; (e) stromal structure; (f) epithelium; (g) hydrophilic GAG's structure; (h) crosslinking between lamellar layers; and (i) fibril structure at the limbus (circumferential ring). The individual data considered necessary for constructing the correct finite element consists of (a) topographic elevation data; (b) wavefront data; and (c) IOP data. Once the correct values of Young's Modulus and Poisson's Ratio are determined, a correct finite element can be constructed. Preferably, the finite element will be a three-dimensional, anisotropic, layered, solid element having 20 nodes. Once the finite element is constructed, an invasive procedure can be simulated and the modeling results compared with empirical data from actual surgical outcomes. The finite element can then be iteratively modified until simulated procedures match observed responses. The output of the optimized model then provides a best predictive instruction for a proposed surgical ophthalmic correction.

Cornea Finite Element Model

Figure 17:
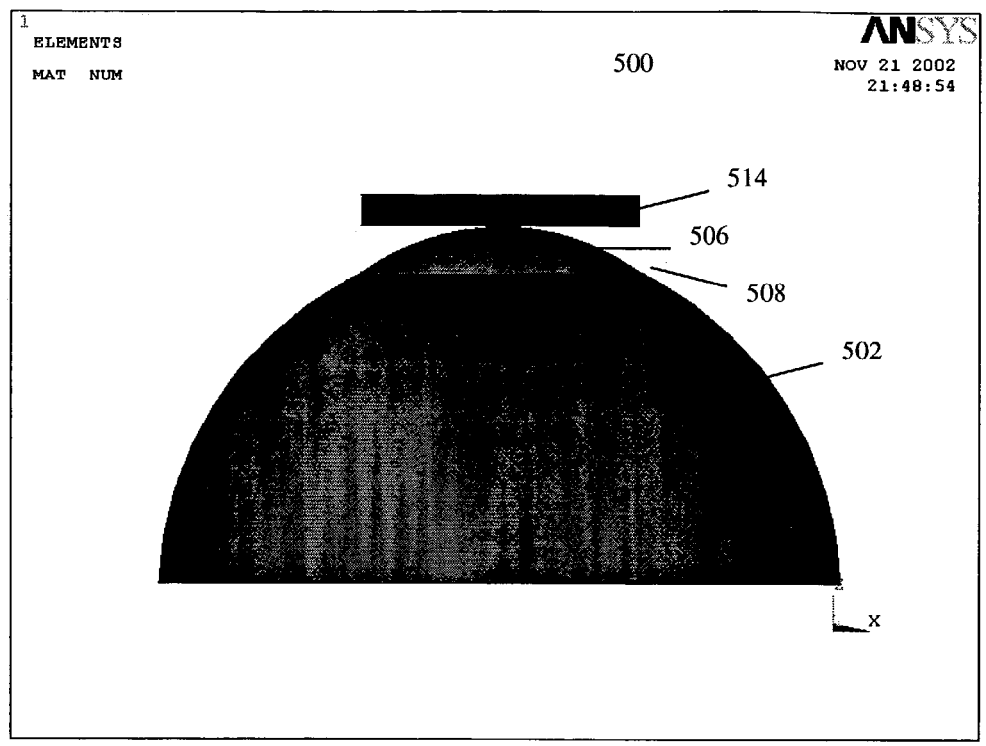
FIG. 17 is a computer simulation of a finite element model of the eye according to an embodiment of the invention.
Figure 18:
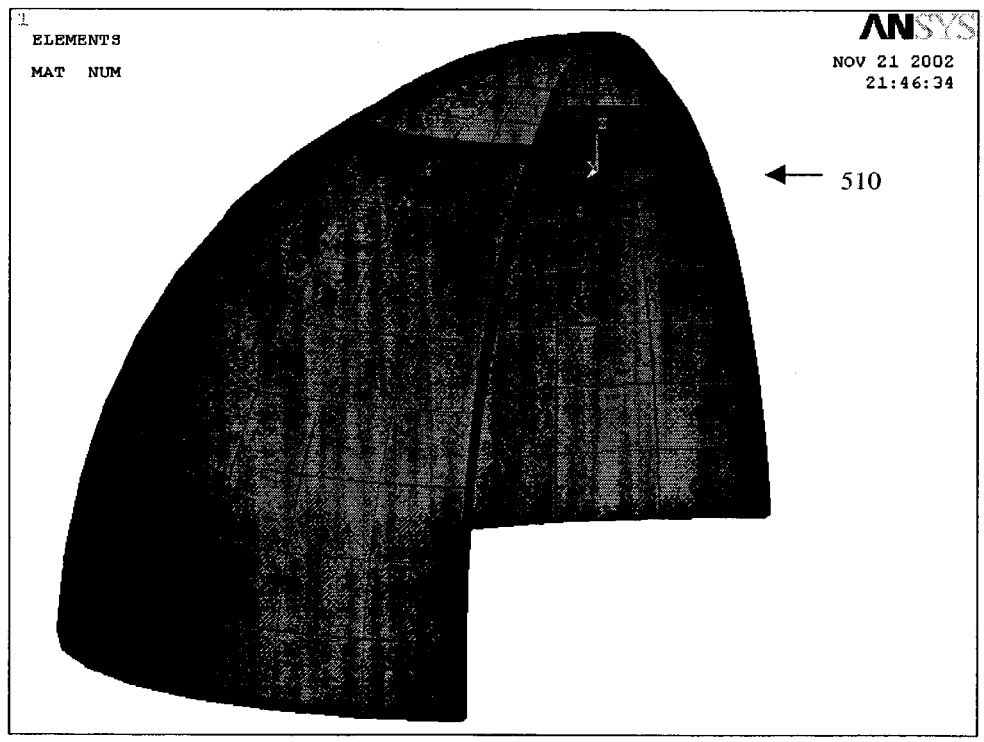
FIG. 18 is a computer simulation of a finite element mesh according to an embodiment of the invention.

According to an illustrative embodiment of the invention, a cornea simulation model 500 shown in FIG. 17 includes the sclera 502, limbus 504, and cornea 506, where corneal anterior/posterior surfaces in the optic zone were determined from diagnostic examinations made with an Orbscan corneal analysis system (Bausch & Lomb Inc., Rochester, N.Y.). The sclera, limbus, and peripheral regions of the cornea are assumed to form an elliptical shape which transitions to the measured cornea surfaces at the edge of the optic zone. FIG. 18 shows a cut-away finite element mesh 508 of the corneal model.

Figure 19:
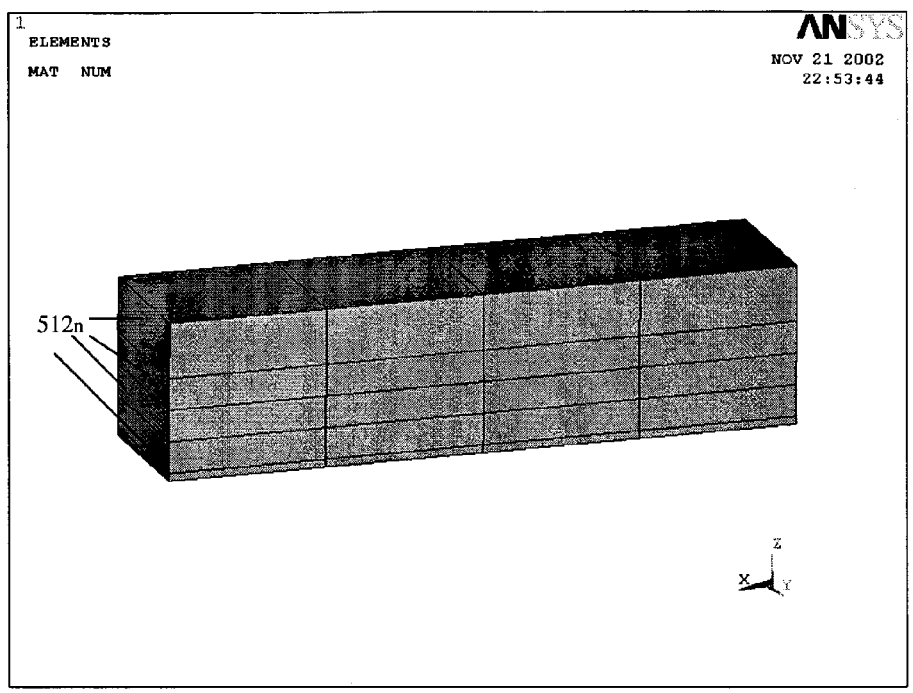
FIG. 19 is a computer simulation of layered solid elements of a finite element model according to an embodiment of the invention.
Figure 20:
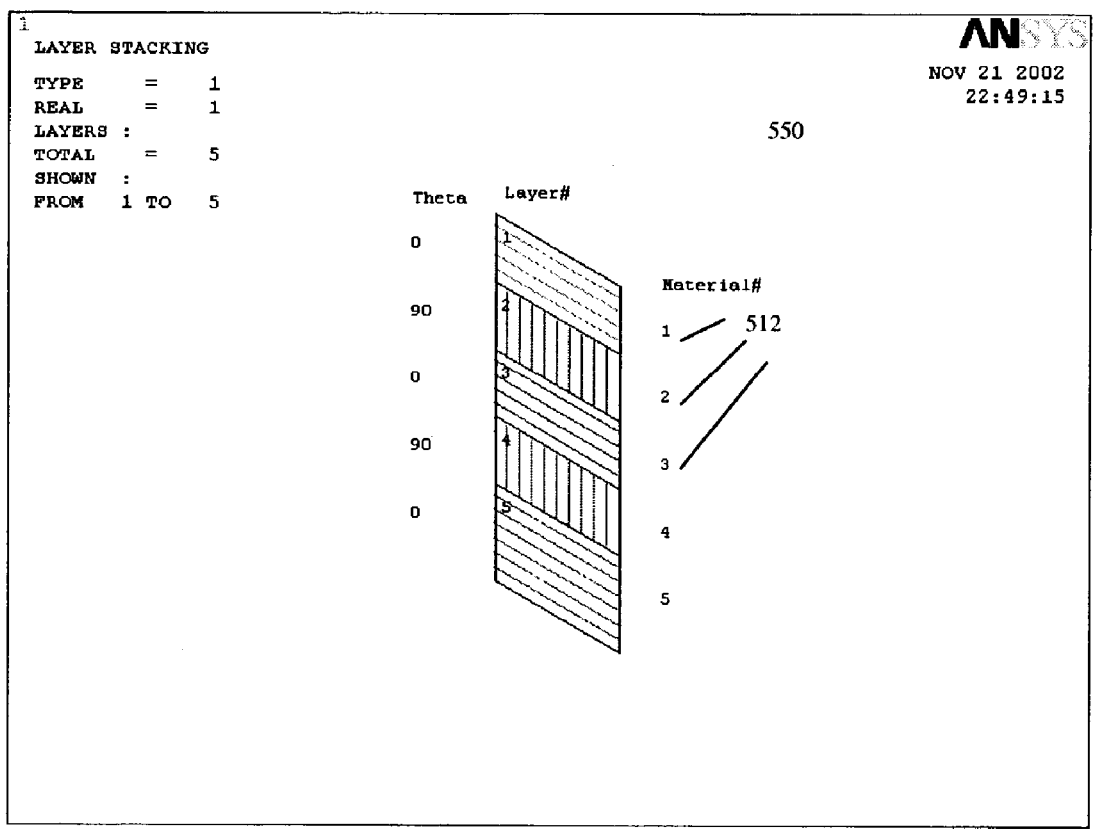
FIG. 20 is a schematic two-dimensional illustration of layered elements of a finite element model according to an embodiment of the invention.

As illustrated in FIG. 19, orthotropic layered brick elements 510 are used to represent all regions of the eye, where the material properties and material orientations for each layer $512_n$ serve to define the gross properties of each region. In the sclera, the layer properties are uniform and give rise to a transversely isotropic response, while the lamella in the limbus have a dominant circumferential orientation and high hoop stiffness. The cornea lamellae have random orientations near the posterior surface, and transition to more predominantly orthogonal orientations near the anterior surface. These orientations are illustrated by the five layered elements $512_1$–$512_5$ shown by the element representation 550 in FIG. 20.

The material properties for each finite element layer (maximum of 100 layers per element, with 5–10 elements through the cornea thickness) must be specified as either a) epithelium, b) Bowman's layer, c) lamella, d) ground substance, e) Decemet's Membrane, or f) endothelium with a prescribed orientation and structure. Truncated normal distributions are used to sample the layer thicknesses as well as the lamella width and orientations; a bilinear weighting function is used to modify the lamellae orientations as a function of depth below the anterior surface. In regions where a simulated lamella would coincide with previously defined lamella, that portion of the layered element is assumed to consist of ground substance. Further, the lamellae are assumed to extend from limbus to limbus along meridians, with thickness variations consistent with constant cross sectional area. The parameters of the sampling distributions can be chosen to represent a broad range of assumptions regarding lamella geometry and the layered lamella interactions.

Figure 21:
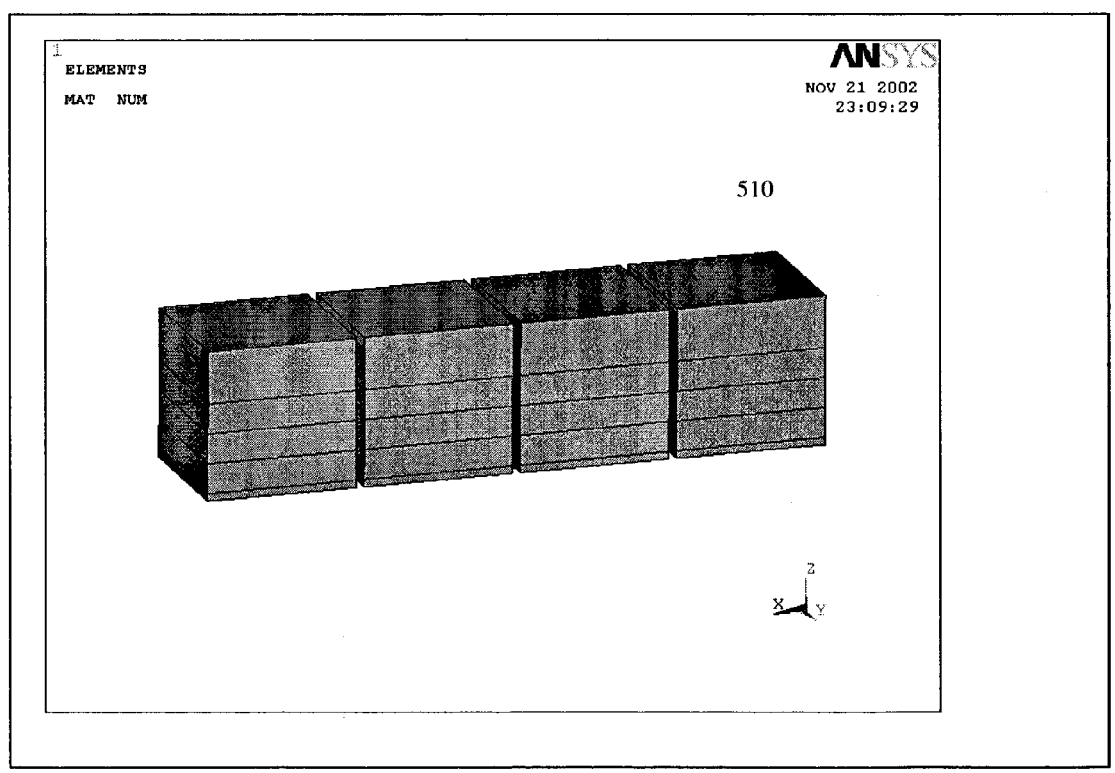
FIG. 21 is a computer simulation of layered solid elements similar to FIG. 19 showing de-coupled segments.

The basic structural load on the cornea is the IOP, and this tends to inflate the eyeball. Therefore, the element formulation incorporates a stress stiffening effect to account for internal pressure. Nonlinear geometrical effects are also included in the evaluation of the finite element response. Further, incisions between finite elements can be simulated by releasing the connectivity between elements that are adjacent to an incision surface. This is accomplished by defining duplicate nodes along potential incision surfaces, and mathematically tying them together. The actual incision is then simulated by releasing the ties sequentially. An example of decoupling the elements is illustrated in FIG. 21.

Figure 22:
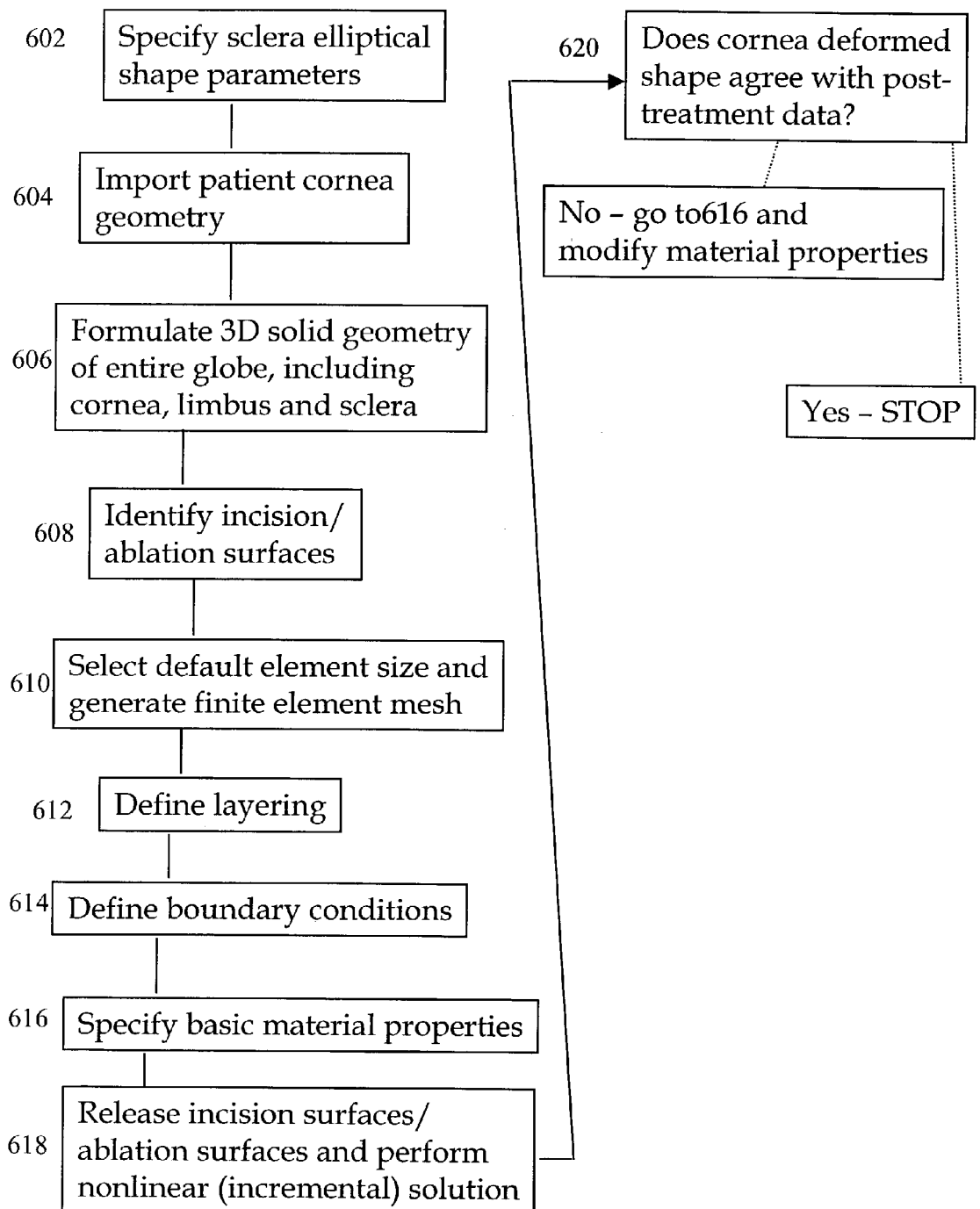
FIG. 22 is a flow diagram according to a method embodiment of the invention.
Figure 23:
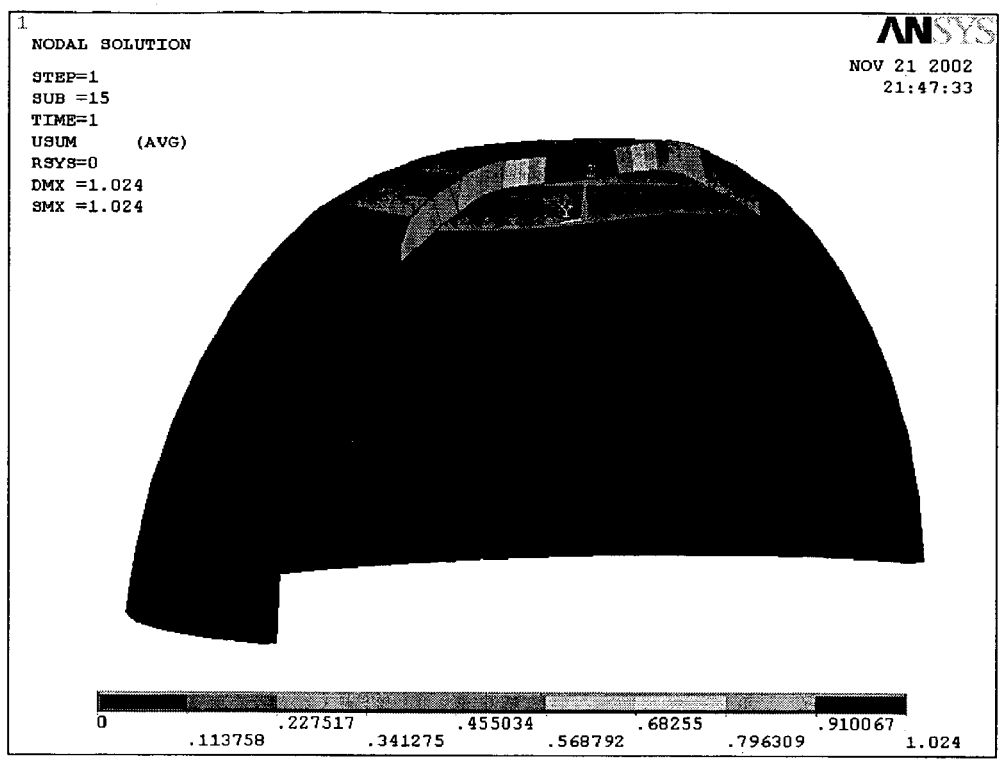
FIG. 23 is a cut-away view computer simulation of an applanated cornea according to an embodiment of the invention.
Figure 24:
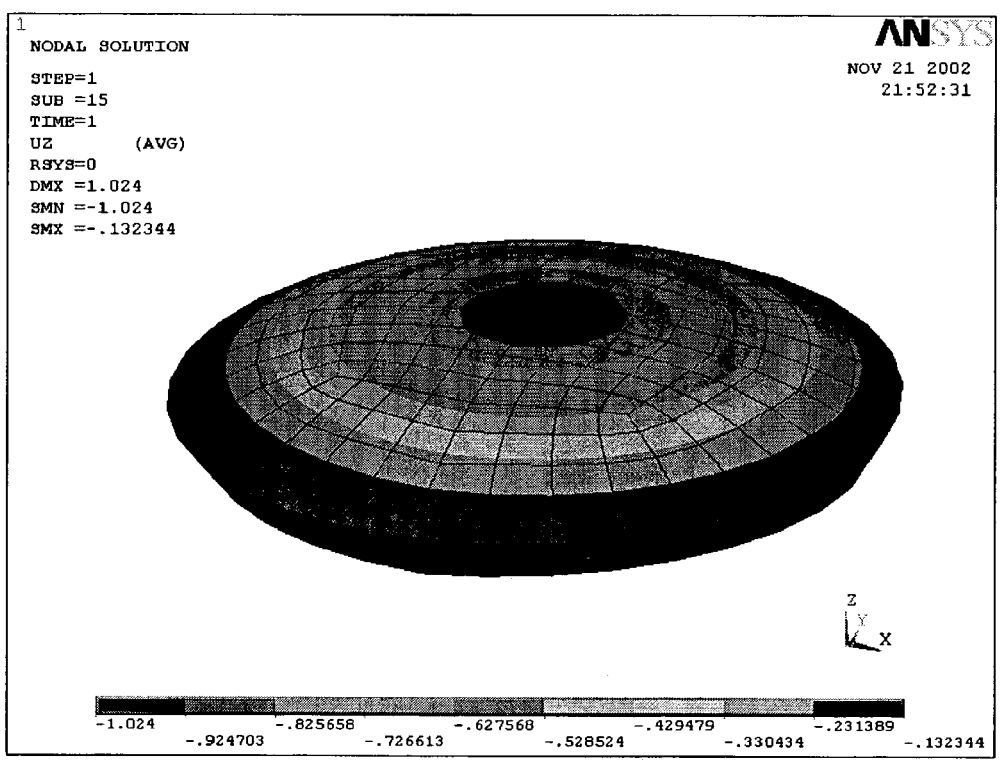
FIG. 24 is a close-up view of the applanated region in FIG. 23.

According to a preferred embodiment of the invention, the finite element analysis approach involves the inclusion of all of the structural properties and observed behaviors of the human cornea combined with additional data on the structure of the human eye. Combining this information with specific information from a patient, the structural observations are then incorporated into a 3D model of a patient's eye. The problem then reduces to solving equations of the form F=Ma+Cv+kx, where M is the mass of the object, a is the acceleration of the object, C is the damping constant for internal oscillations, v is velocity, k is the stiffness matrix for the elastic deformation of the material and x is the magnitude of the displacement. The equation contains all of the information necessary to predict the mechanical behavior of the human cornea. The equation may become non-linear, in which case the mathematics become more complicated. The actual solution of these equations will require the solution of a system of non-linear partial differential equations (PDE's). The differential equations will be solved by finding a solution to the weak form of the PDE's. It will be appreciated, however, that the mathematics required to solve the corneal problem are identical to the mathematics to solve any material deformation problem. The embodiment of the invention, then, is the constitutive relationships which are dependent upon the constitutive properties that are created inside of elements and between elements. If one knows the constitutive properties of the elements, a solution can be found for the corneal response system. This instant embodiment is designed to back calculate corneal constitutive properties for classes of patients and provide predictive analysis of the cornea structural response due to any action asserted upon the cornea. An exemplary method of obtaining these constitutive properties is illustrated in the flow diagram 600 of FIG. 22. In step 602, sclera elliptical shape parameters are specified. These parameters can be obtained from axial length measurements of the eye, or generalized values from the normal population may be used. At step 604, patient cornea geometry is determined. Preferably, this is anterior chamber geometry and most preferably, this is in the form of non-uniform rational basis splines (NURBS) obtained with an Orbscan pre-treatment examination. In alternative aspects, appropriate data could be obtained by OCT or C-scan (ultrasound) measurements. At step 606, a 3D solid geometry of the entire globe including cornea, limbus and sclera is formulated (as illustrated in FIGS. 17, 18. In step 608, the incision/ablation surfaces are identified based upon a best estimate of a prospective surgical plan. Applanation of the cornea is simulated with applanation plate 514 of FIG. 17, and a 1 mm deformed cornea is illustrated in cut-away and enlarged in FIGS. 23 and 24, respectively. At step 610, default finite element size is selected and a finite element mesh is generated as illustrated in FIG. 18. A spherical element coordinate system is used, and the element edges coincide with the incision/ablation surfaces. In essence, the elements are built around the intended incisions with the ability to couple and de-couple the elements at those locations. At step 612, the element layers are defined. The process for each layer is as follows:

(a) Specify material as epithelium, Bowman's layer, lamella, ground substance, Decemet's Membrane, or endothelium,
(b) Specify layer thickness,
(c) Specify lamella locations and orientations for this layer, by
   i) selecting a starting point on circumference (0 to 360 degrees),
   ii) selecting a lamella orientation (−90 to 90 degrees; function of depth),
   iii) selecting lamella width (1 to 4 mm),
   iv) projecting each lamella from limbus-to-limbus;
   v) if clear or partially blocked by another lamella in this layer, reduce width and complete projection; otherwise, define as ground substance
   vi) have maximum number of lamellae been processed? If No—go to (c);
       If Yes—define all unspecified layers as ground substance
       and continue to next layer.
   vii) after ground substance and lamella properties have been defined for all layers, apply to individual elements based on location of element centroids.

At step 612, the boundary conditions are defined. These preferably include a displacement constraint at the sclera, and individualized IOP values. At step 616, the basic material parameters of the system are specified. These include Young's moduli ($E_x$, $E_y$, $E_z$); Poisson's Ratio ($v_{xy}$, $v_{yz}$, $v_{xz}$); and shear moduli ($G_{xy}$, $G_{yz}$, $G_{xz}$). At step 618, the incision/ablation surfaces are released and an incremental non-linear solution is performed. Finally, at step 620, the modeled corneal shape is compared with measured post-treatment data. If the shapes are in agreement, then the finite element is modeled correctly. If the shape agreement is not satisfactory, then the method returns to step 616 where the material parameters are modified and steps 618, 620 are reiterated.

The end result of the modeling is an accurate finite element model for each "class" of patients that can then be used as predictive information when a new patient in a particular patient class is evaluated for surgery, according to the invention.

Figure 2:
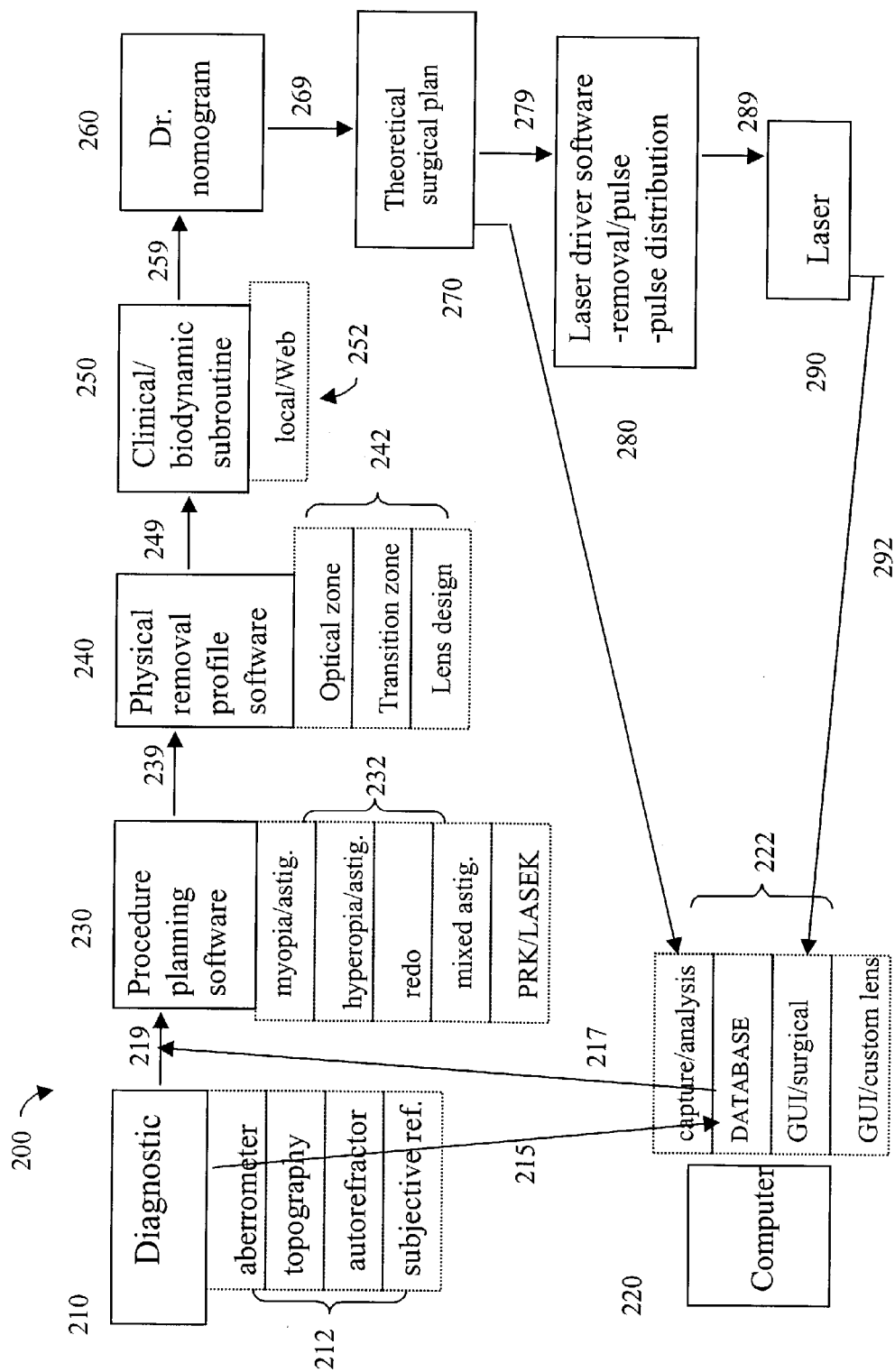
FIG. 2 is a block diagram of a system according to another preferred embodiment of the invention.

FIG. 2 illustrates an overall system configuration 200 for a LASIK procedure that incorporates the invention as described in the foregoing embodiments. A diagnostic station 210 preferably incorporates an aberrometer for wavefront measurement, and may also include any suitable diagnostic instrumentation 212 as shown, for example, a topography device for measuring corneal geometry, an autorefractor or other device for objective or subjective refraction data, a tonometer for IOP, and others known in the art. The diagnostic output 215, representing "new" information about a patient is sent to a computer 220 that includes structural and functional architectures 222 such as an optimized actual and theoretical historical outcomes database, capture/analysis software, graphical user interfaces (GUIs) for surgical and custom lens applications, and others (not shown). Analysis of the diagnostic information 215 in conjunction with the historical information is provided in the form of a best predictive outcome instruction 217 which is integrated at 219 with procedure planning software 230. A non-exhaustive nor limiting list of corrective procedures 232 includes myopia, myopic astigmatism, hyperopia, hyperopic astigmatism, re-do (e.g., prior decentered ablation), mixed astigmatism, PRK, LASEK, etc. This information is then integrated at 239 with physical removal profile software 240 that may take into account factors 242 such as, e.g., optical zone size, transition zone size, custom contact lens design, etc. The information is further integrated at 249 with other clinical and biodynamic modifications 250 that can be accessed locally or over the internet, for example, as shown at 252. The information is still further modified at 259 by personalized surgeon nomogram 260. All of this analyzed information is then used at 269 to generate a theoretical surgical plan 270 which is sent at 279 to the laser driver software 280 for driving the therapeutic laser 290. Such a system is embodied, for example, in the Bausch & Lomb Incorporated Zyoptix® system incorporating the Zylin® version 2.40 algorithm package. As shown, the optimized theoretical surgical plan 270 and the actual historical outcome data 292 are used to continually update the data structure 220 to provide the best predictive outcome instruction for the corrective procedure.

Figure 3:
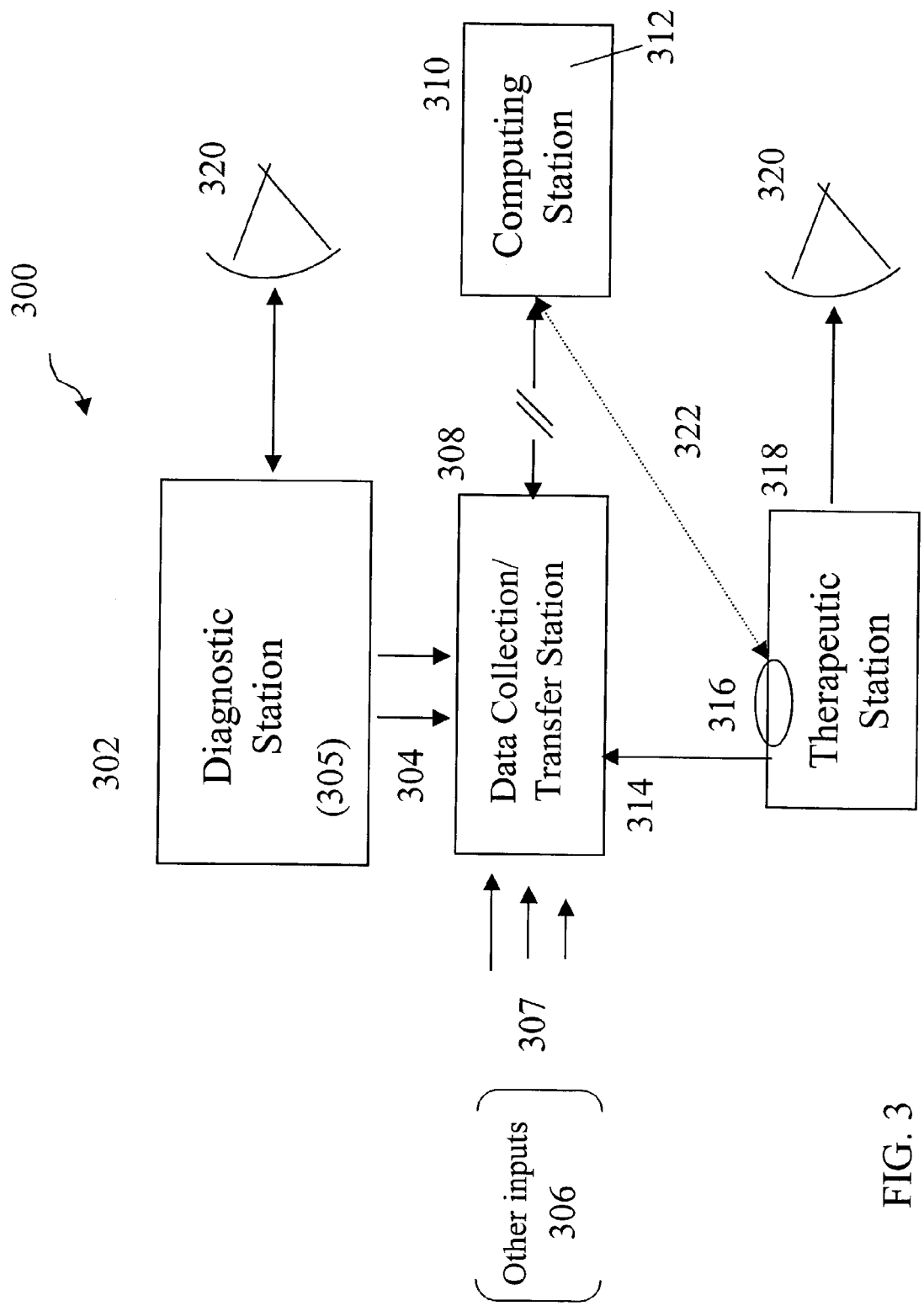
FIG. 3 is a block diagram of an exemplary LASIK system in accordance with the invention.

Another embodiment of the invention representing a system 300 for providing a predictive outcome for an ophthalmic therapeutic correction, such as a photoablative corneal reshaping, is illustrated by the block diagram of FIG. 3. A diagnostic station 302 is provided to obtain new measurements about the ophthalmic condition of a patient's eye 320. The diagnostic station 302 preferably will consist of one or more diagnostic devices including, for example, a wavefront sensor, topography instrumentation, an optical coherence tomography (OCT) system, an ultrasound device, a scanning laser ophthalmoscope (SLO), and/or others used alone or in combination as will be appreciated by a person skilled in the art. The diagnostic station will have the capability to export a new information metric 305 acquired by its particular diagnostic capabilities. A data collection and transfer station 308 is appropriately connected to the diagnostic station 302 for receiving the new diagnostic input 305 at 304. The data collection and transfer station 308 is also adapted to optionally receive different, new prospective therapeutic-outcome-influencing information 306 than that provided by the diagnostic station 302, as shown by arrows 307. This information might include patient profile data, practitioner data, environmental data, and so on, and could be input to station 308 manually via keypad or CD, for example, or automatically by appropriate sensors that record the desired information. The data collection and transfer station 308 is further connected to a computing station 310 that is similar in form and function to computing station 110 described above in connection with FIG. 1. A therapeutic station 318, preferably comprising a flying spot, excimer laser system and eyetracker is also communicatively connected to the data collection and transfer station 308 to receive output 314 or, alternatively, to computing station 310 to receive output 322. Regardless of whether station 308 or station 310 is the source of the ultimate output 316, that output will be a best predictive instruction, preferably in the form of a custom photoablative algorithm for driving the therapeutic laser system, for facilitating correction of the patient's vision defects. As before, various stations can be located locally or remotely as appropriate for gathering information and carrying out procedures contemplated by the invention. As will be appreciated, the best predictive instruction, which is the ultimate result of the invention disclosed herein, may be used to drive custom contact lens, IOL, inlay, or onlay fabrication.

In an alternative embodiment, the invention is directed to an executable instruction, embodied in a deliverable means to an end user to provide a predictive outcome for a therapeutic ophthalmic correction or ophthalmic optic as described above. The instruction could be delivered as a surgical parameter, for example, a LASIK keratectomy depth, or an optical zone size recommendation for photoablative surgery, and executed by practice of a practitioner, or as a custom contact lens or IOL prescription. In a related aspect, the instruction could be delivered via a computer or device-readable medium or means such as, but not limited to, a disk, CD, land or satellite-based data stream, etc., and executed upon command as, for example, an ablation shot profile or ablation algorithm for a therapeutic laser system.

Figure 10:
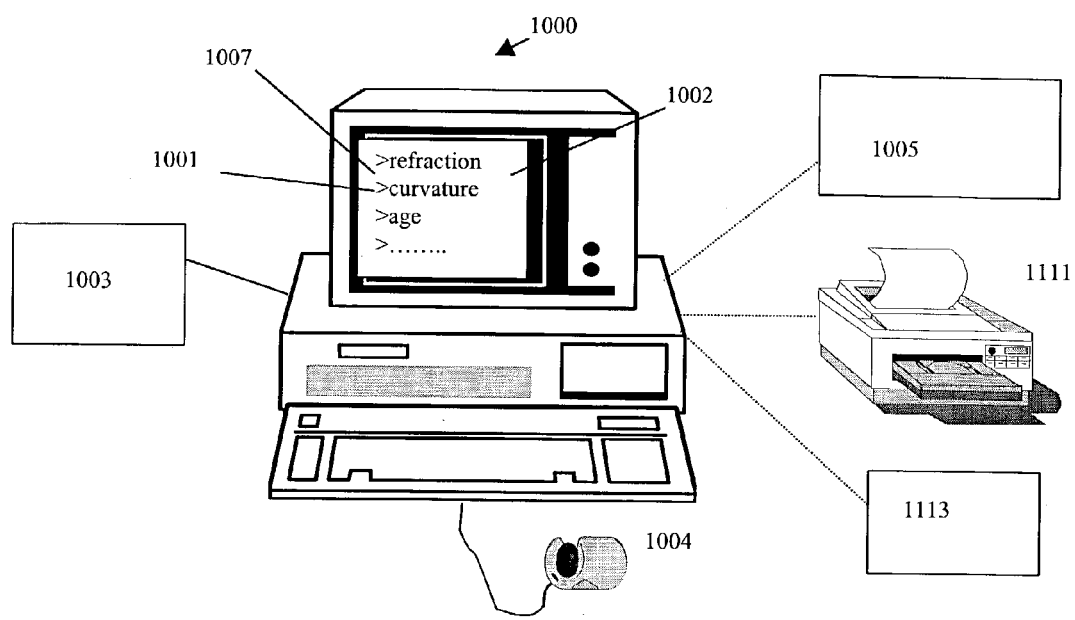
FIG. 10 is a diagram illustrating a hardware related embodiment of the invention.

In another embodiment illustrated with reference to FIG. 10, the invention is directed to an ophthalmic diagnostic and/or treatment system 1000 including diagnostic 1003 and/or treatment 1005 components, including a graphical user interface 1001 having a display 1002 and a selection device 1004 that facilitates the selection of collected information for analysis with a data structure of optimized historical information resulting in an outcome-predictive instruction for effecting a vision correction procedure. In the system 1000 according to the invention, a method of providing and selecting from a menu 1007 on the display 1002 comprises the following steps: a) retrieving a set of menu entries from the menu 107, each of the menu entries representing a prospective, ophthalmic, therapeutic outcome-influencing characteristic; b) receiving a menu entry selection signal indicative of the selection device pointing at a selected menu entry from the set of menu entries; and c) in response to the signal, engaging an analysis of a selected menu entry in conjunction with a data structure of optimized actual and theoretical historical information, wherein the analysis generates a best predictive instruction relating to an outcome for an ophthalmic therapeutic correction or lens design.

Figure 4:
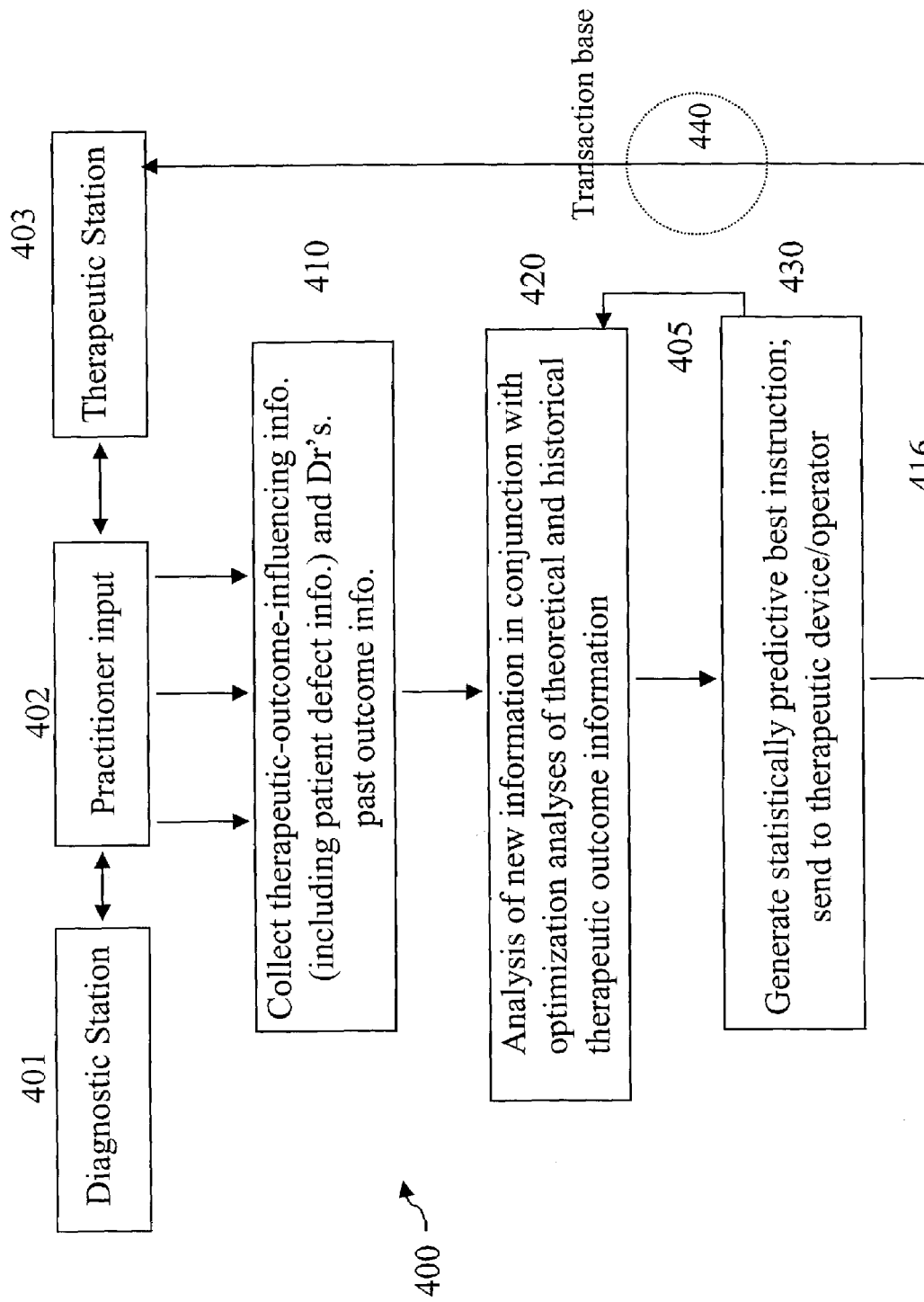
FIG. 4 is a block diagram/flow chart illustrating a method according to an embodiment of the invention.

FIG. 4 describes in flow chart manner the process 400 generally performed by the systems 100, 200, 300, 1000 shown in FIGS. 1, 2, 3, and 10, respectively. At block 410, a plurality of prospective and known therapeutic-outcome-influencing new information is collected from various sources 401, 402, 403. This new information includes the patient's ophthalmic defect information and a variety of other information relating to the patient, the practitioner, the diagnostic and therapeutic instrumentation, and the local environment, for example. At block 420, optimized (statistically or otherwise), historical, therapeutic-outcome information is stored along with theoretical surgical plan information 405. The new information pertaining to the correction of the patient's vision defect is analyzed in conjunction with the historical, optimized therapeutic-outcome information. At block 430, a best predictive instruction 416 is generated and delivered to the therapeutic device/operator 403. Preferably, the best predictive instruction is an optimized, custom photoablative algorithm (but not necessarily so limited) that is implemented to drive the laser system and provide the desired patient vision correction. The instruction may be optimized by statistical analyses, multi-variable matrix calculations, neural network processing, and/or other methods known to those skilled in the art.

In an aspect of the method embodiment, a best predictive instruction is provided to a practitioner by a third party on a fee based or transaction basis as shown at 440. Typically, individual surgeons throughout the world are limited to a historical outcome base proprietary to their own practice. While this, arguably, may be sufficient for a very high-volume practice, it would be advantageous for a surgeon to have access to a vastly larger database of optimized, historical outcome information as a resource for providing vision correction treatments. Such a database may be owned, for example, by a third party, who may make the database information available to practitioners (and others) for a fee or other consideration. Historical database entries may be obtained by the database owner from other third parties for a fee or other consideration. This is advantageous for expanding and updating the historical outcome database. A third party database owner could provide to a practitioner an optimized, outcome-predictive instruction (e.g., ablation algorithm for driving a photoablative laser system), on a remunerative basis, in response to the practitioner's request for such an instruction based on the patient's ophthalmic defect and other relevant outcome-influencing information provided to the third party owner by the practitioner. Data supplied by the practitioner could be acquired manually and/or automatically and transmitted to a third party who would analyze the information in conjunction with their large outcomes database (preferably many thousands of cases). The third party owner would then transmit an optimized, outcome-predictive instruction to the practitioner that should provide an optimized visual outcome for the patient. Depending on the practitioner's equipment, he/she may use the optimized instruction provided by the third party to simulate the prospective treatment so that the patient would know in advance of surgery what the patient's postoperative vision should be like, or in other ways, including performing ophthalmic surgery. This simulation could be presented in various textual, graphical, or other visual forms provided by the GUI 1001 or printer 1111, for example, or by a phoropter device 1113 with a deformable mirror or other phase compensation means known in the art, as shown in FIG. 10.

While various advantageous embodiments have been chosen to illustrate the invention, it will be understood by those skilled in the art that changes and modifications can be made therein without departing from the scope of the invention as defined in the appended claims.

We claim:

1. A system that provides a predictive outcome for a proposed therapeutic ophthalmic correction, comprising:
   a collecting and transmitting station for collecting a prospective, therapeutic-outcome-influencing, new information metric relating to at least one of a patient, a practitioner, a diagnostic measurement, a therapeutic condition, and an environmental condition, and for transmitting said plurality of new information to a computing station, wherein said computing station includes means for
   a) receiving said new information metric,
   b) storing a plurality of optimized historical therapeutic-outcome information derived from an optimization analysis of prospective therapeutic-outcome-influencing, historical information relating to at least one of a patient, a practitioner, a diagnostic measurement, a therapeutic condition, and an environmental condition, and
   c) providing an output comprising a predictive best instruction that is derived from an analysis of the new information in conjunction with the optimized historical information to facilitate an improved therapeutic ophthalmic correction.

2. The system of claim 1, wherein the predictive best instruction is an algorithm that describes a laser ablation shot placement pattern on a patient's eye.

3. The system of claim 1, wherein the predictive best instruction comprises an outcome-predictive, ophthalmic information metric suited for use by a practitioner for providing the therapeutic ophthalmic correction.

4. The system of claim 1, wherein the optimization analysis is a statistical analysis.

5. The system of claim 1, wherein the optimization analysis is a matrix analysis comprising a vector, Z, representing new diagnostic information, a clinical matrix, M', representing an interdependence relationship of a plurality of Zernike terms or their equivalents, another matrix, M", representing historical outcome information, and a resultant matrix, Z', representing the predictive best instruction.

6. The system of claim 5, further comprising a feedback loop provided by an updating information metric supplied to the matrix M".

7. The system of claim 5, wherein the components of M" represent information from a plurality of sources.

8. The system of claim 5, wherein the components of Z are Zernike vectors or their equivalents output from a wavefront sensor device.

9. The system of claim 4, wherein the computing station comprises a data structure employing a neural network for generating the predicted best instruction.

10. The system of claim 1, wherein the predicted best instruction is a postoperative spherical aberration value, $Z_{400Post}$, for a given pupil size.

11. The system of claim 10, wherein the postoperative spherical aberration value, $Z_{400Post}$, is exclusively dependent upon a preoperative spherical aberration value, $Z_{400Pre}$, a preoperative defocus value, $Z_{200Pre}$, and a constant factor, $\pm C$.

12. The system of claim 11, wherein $Z_{400Post}=A*Z_{400Pre}+B*Z_{200Pre}+C$, where A, B are ($\pm$) constants for the given pupil size.

13. The system of claim 1, wherein the computing station is in physical proximity to the collecting and transmitting station.

14. The system of claim 1, wherein the computing station is located remotely from the collecting and transmitting station.

15. A system that provides a predictive outcome for a therapeutic ophthalmic correction, comprising a computing station having a data structure that contains an optimized historical therapeutic-outcome information metric derived from an optimization analysis of a plurality of prospective therapeutic-outcome-influencing, historical information metrics, wherein the computing station is programmed to receive a plurality of prospective therapeutic-outcome-influencing, new information including at least ophthalmic defect information about a patient, wherein said computing station is further programmed to provide in a suitable form an outcome-predictive best instruction based upon an analysis of the new information in conjunction with the historical outcome information.

16. The system of claim 15, wherein the data structure comprises a neural network.

17. The system of claim 15, wherein the outcome-predictive best instruction is an algorithm that describes a laser ablation shot placement pattern on a patient's eye.

18. The system of claim 15, wherein the outcome-predictive best instruction is a postoperative spherical aberration value, $Z_{400Post}$, for a given pupil size.

19. The system of claim 18, wherein the postoperative spherical aberration value, $Z_{400Post}$, is exclusively dependent upon a preoperative spherical aberration value, $Z_{400pre}$, a preoperative defocus value, $Z_{200Pre}$, and a constant factor, $\pm C$.

20. The system of claim 19, wherein $Z_{400Post}=A*Z_{400Pre}+B*Z_{200Pre}+C$, where A, B are ($\pm$) constants for the given pupil size.

21. The system of claim 15, wherein the optimization analysis is a statistical analysis.

22. The system of claim 21, wherein the optimization analysis is a matrix analysis comprising a vector, Z, representing new diagnostic information, a clinical matrix, M', representing an interdependence relationship of a plurality of Zernike terms or their equivalents, another matrix, M", representing historical outcome information, and a resultant matrix, Z', representing the predictive best instruction.

23. The system of claim 22, further comprising a feedback loop provided by an updating information metric supplied to the matrix M".

24. The system of claim 22, wherein the components of M" represent information from a plurality of sources.

25. The system of claim 22, wherein the components of Z are Zernike vectors or their equivalents output from a wavefront sensor device.

26. A system that provides a predictive outcome for a therapeutic ophthalmic correction, comprising:
   a) a diagnostic station that acquires a new, ophthalmic information metric from a patient and export the new information metric;
   b) a data collection and transfer station cooperatively engaged with the diagnostic station that receives and further exports the new information metric;
   c) a computing station communicatively engaged with the data collection and transfer station, said computing station including a data structure containing optimized historical therapeutic-outcome information, programmed to receive and transmit information and to analyze each respective new information metric in conjunction with the optimized historical therapeutic-outcome information and, further, to generate a predictive best instruction; and
   d) a therapeutic station cooperatively engaged with the computing station, having a capability to execute the predictive best instruction.

27. The system of claim 26, wherein the data structure comprises a neural network.

28. The system of claim 26, wherein the outcome-predictive best instruction is an algorithm that describes a laser ablation shot placement pattern on a patient's eye.

29. The system of claim 26, wherein the outcome-predictive best instruction is a postoperative spherical aberration value, $Z_{400Post}$, for a given pupil size.

30. The system of claim 29, wherein the postoperative spherical aberration value, $Z_{400Post}$, is exclusively dependent upon a preoperative spherical aberration value, $Z_{400Pre}$, a preoperative defocus value, $Z_{200Pre}$, and a constant factor, ±C.

31. The system of claim 30, wherein $Z_{400Post}=A*Z_{400pre}+B*Z_{200Pre}+C$, where A, B are (±) constants for the given pupil size.

32. The system of claim 26, wherein the optimization analysis is a statistical analysis.

33. The system of claim 32, wherein the optimization analysis is a matrix analysis comprising a vector, Z, representing new diagnostic information, a clinical matrix, M', representing an interdependence relationship of a plurality of Zernike terms or their equivalents, another matrix, M", representing historical outcome information, and a resultant matrix, Z', representing the predictive best instruction.

34. The system of claim 33, further comprising a feedback loop provided by an updating information metric supplied to the matrix M".

35. The system of claim 33, wherein the components of M" represent information from a plurality of sources.

36. The system of claim 33, wherein the components of Z are Zernike vectors or their equivalents output from a wavefront sensor device.

37. A method for providing a predictive outcome for a therapeutic ophthalmic correction, comprising:
   a) collecting a therapeutic-outcome-influencing, new information metric including at least ophthalmic defect information about a patient;
   b) analyzing said new information in conjunction with a plurality of optimized, historical therapeutic outcome information for the determined ophthalmic defect; and
   b) generating, via the computing device, a predictive best instruction for facilitating an optimized outcome of the ophthalmic therapeutic correction.

38. The method of claim 37, further comprising utilizing the generated predictive best instruction to drive a therapeutic system for providing the ophthalmic correction.

39. The method of claim 37, wherein the collecting step comprises automatically collecting the new information metric.

40. The method of claim 37, wherein the generating step comprises a statistical analysis.

41. The method of claim 37, wherein the generating step comprises calculating a resultant matrix, Z', representing the predictive best instruction, from a vector, Z, representing the new diagnostic information, a clinical matrix, M', representing an interdependence relationship of a plurality of Zernike terms or their equivalents, and another matrix, M", representing the historical outcome information.

42. A method for providing a predictive outcome for a therapeutic ophthalmic correction, comprising:
   a) obtaining a new information metric, said new information metric relating to an ophthalmic defect condition of a patient;
   b) maintaining a database of optimized, historical ophthalmic outcome information, said ophthalmic outcome information being related to the ophthalmic defect condition; and
   c) providing a predictive best instruction for the therapeutic ophthalmic correction, wherein the predictive best instruction is provided on a transactional basis.

43. The method of claim 42, wherein the step of obtaining a new information metric comprises collecting wavefront aberration data from a wavefront sensor device.

44. The method of claim 42, wherein the step of maintaining a database of optimized, historical ophthalmic outcome information comprises updating the database with available ophthalmic correction outcome information and optimizing the historical outcome information.

45. The method of claim 42, wherein optimizing the historical outcome information comprises a statistical analysis of the historical outcome information.

46. The method of claim 45, wherein optimizing the historical outcome information comprises engaging a neural network to analyze the historical outcome information and the available historical outcome information.

47. The method of claim 42, wherein the step of maintaining a database of optimized, historical ophthalmic outcome information comprises acquiring new historical outcome information from a third party for a fee.

48. The method of claim 42, wherein the step of providing a predictive best instruction on a transactional basis comprises receiving a fee or other remuneration.

49. A computer-readable or device-readable medium having stored thereon an executable instruction that is intended to provide a predictive outcome for a therapeutic ophthalmic correction, wherein said instruction is a predicted best instruction that is derived from an analysis of a new information metric relating to an ophthalmic condition of a patient, in conjunction with an optimized, historical, therapeutic-outcome information metric.

50. The medium of claim 49, wherein the executable instruction is an algorithm that describes a laser ablation shot placement pattern on a patient's eye.

51. The system of claim 49, wherein the predictive best instruction comprises an outcome-predictive, ophthalmic information metric suited for use by a practitioner for providing the therapeutic ophthalmic correction.

52. A data structure associated with a computing device that generates a predictive best instruction for a therapeutic ophthalmic correction, said data structure performing a method comprising the steps of:
  a) receiving a new information metric, said new information metric relating to an ophthalmic defect condition of a patient;
  b) maintaining a database of optimized historical ophthalmic outcome information, said ophthalmic outcome information being related to the ophthalmic defect condition; and
  c) generating a predictive best instruction for the therapeutic ophthalmic correction.

53. The data structure of claim 52, wherein the predictive best instruction is provided on a transactional basis.

54. The data structure of claim 53, wherein the step of providing a predictive best instruction on a transactional basis comprises receiving a fee or other remuneration.

55. The data structure of claim 52, wherein the step of obtaining a new information metric comprises collecting wavefront aberration data from a wavefront sensor device.

56. The data structure of claim 52, wherein the step of maintaining a database of optimized, historical ophthalmic outcome information comprises updating the database with available ophthalmic correction outcome information and optimizing the historical outcome information.

57. The data structure of claim 56, wherein optimizing the historical outcome information comprises a statistical analysis of the historical outcome information.

58. The data structure of claim 56, wherein optimizing the historical outcome information comprises engaging a neural network to analyze the historical outcome information and the available historical outcome information.

59. The data structure of claim 52, wherein the step of maintaining a database of optimized, historical ophthalmic outcome information comprises acquiring new historical outcome information from a third party for a fee.

60. The system of claim 1, wherein the optimization analysis is a finite element analysis (FEA) utilizing a finite element model (FEM), further wherein the FEM is a three-dimensional, anisotropic, nonlinear, viscoelastic layered element.

61. The system of claim 15, wherein the optimization analysis is a finite element analysis (FEA) utilizing a finite element model (FEM), further wherein the FEM is a three-dimensional, anisotropic, nonlinear, viscoelastic layered element.

62. The system of claim 26, wherein the optimization analysis is a finite element analysis (FEA) utilizing a finite element model (FEM), further wherein the FEM is a three-dimensional, anisotropic, nonlinear, viscoelastic layered element.

63. The method of claim 37, wherein the generating step comprises performing a finite element analysis (FEA) utilizing a finite element model (FEM), further wherein the FEM is a three-dimensional, anisotropic, nonlinear, viscoelastic layered element.

* * * * *